United States Patent
Grammenos et al.

(10) Patent No.: US 11,425,910 B2
(45) Date of Patent: Aug. 30, 2022

(54) SUBSTITUTED OXADIAZOLES FOR COMBATING PHYTOPATHOGENIC FUNGI

(71) Applicant: BASF SE, Ludwigshafen am Rhein (DE)

(72) Inventors: Wassilios Grammenos, Ludwigshafen (DE); Violeta Terteryan-Seiser, Ludwigshafen (DE); Maria Angelica Quintero Palomar, Limburgerhof (DE); Ian Robert Craig, Ludwigshafen (DE); Christine Wiebe, Ludwigshafen (DE); Tobias Mentzel, Limburgerhof (DE); Marcus Fehr, Limburgerhof (DE); Ana Escribano Cuesta, Ludwigshafen (DE); Christian Harald Winter, Navi Mumbai (IN); Jan Klaas Lohmann, Ludwigshafen (DE); Bernd Mueller, Ludwigshafen (DE); Thomas Grote, Ludwigshafen (DE); Erica Cambeis, Ludwigshafen (DE); Michael Seet, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 400 days.

(21) Appl. No.: 16/487,121

(22) PCT Filed: Feb. 13, 2018

(86) PCT No.: PCT/EP2018/053553
§ 371 (c)(1),
(2) Date: Aug. 20, 2019

(87) PCT Pub. No.: WO2018/153730
PCT Pub. Date: Aug. 30, 2018

(65) Prior Publication Data
US 2021/0137115 A1    May 13, 2021

(30) Foreign Application Priority Data
Feb. 21, 2017   (EP) ..................................... 17157051

(51) Int. Cl.
*A01N 43/82*     (2006.01)
*C07D 271/06*    (2006.01)
*A01P 3/00*      (2006.01)
*A01N 47/12*     (2006.01)

(52) U.S. Cl.
CPC ............. *A01N 43/82* (2013.01); *A01N 47/12* (2013.01); *A01P 3/00* (2021.08); *C07D 271/06* (2013.01)

(58) Field of Classification Search
CPC .............................. C07D 271/06; A01N 43/82
See application file for complete search history.

(56) References Cited

FOREIGN PATENT DOCUMENTS

| | | |
|---|---|---|
| EP | 0276432 A2 | 8/1988 |
| JP | 2020-23442 * | 2/2020 |
| WO | WO-97/30047 A1 | 8/1997 |
| WO | WO-97/40688 A1 | 11/1997 |
| WO | WO-2015/185485 A1 | 12/2015 |
| WO | WO-2016/055404 A1 | 4/2016 |
| WO | WO-2016/142224 A1 | 9/2016 |
| WO | WO-2016/156129 A1 | 10/2016 |
| WO | WO-2016/166020 A1 | 10/2016 |
| WO | WO-2017/016915 A1 | 2/2017 |
| WO | WO-2017/018803 A1 | 2/2017 |
| WO | WO-2017/055587 A1 | 4/2017 |
| WO | WO-2017/060148 A1 | 4/2017 |
| WO | WO-2017/067784 A1 | 4/2017 |
| WO | WO-2017/076739 A1 | 5/2017 |
| WO | WO-2017/076740 A1 | 5/2017 |
| WO | WO-2017/076742 A1 | 5/2017 |
| WO | WO-2017/076757 A1 | 5/2017 |
| WO | WO-2017/076935 A1 | 5/2017 |
| WO | WO-2017/081309 A1 | 5/2017 |
| WO | WO-2017/081310 A1 | 5/2017 |
| WO | WO-2017/081311 A1 | 5/2017 |
| WO | WO-2017/081312 A1 | 5/2017 |
| WO | WO-2017/085098 A1 | 5/2017 |
| WO | WO-2017/085100 A1 | 5/2017 |
| WO | WO-2017/093019 A1 | 6/2017 |
| WO | WO-2017/093120 A1 | 6/2017 |
| WO | WO-2017/093167 A1 | 6/2017 |
| WO | WO-2017/148797 A1 | 9/2017 |
| WO | WO-2017/178245 A1 | 10/2017 |

(Continued)

OTHER PUBLICATIONS

Machine translation of WO 2018/117034 (Jun. 2018).*

(Continued)

*Primary Examiner* — John Pak
(74) *Attorney, Agent, or Firm* — Marshall, Gerstein & Borun LLP

(57) ABSTRACT

The present invention relates to novel trifluoromethyloxadiazoles of the formula I, or the N-oxides, or the agriculturally useful salts thereof; and to their use for controlling phytopathogenic fungi; and to a method for combating phytopathogenic harmful fungi, which process comprises treating the fungi, the plants, the soil or seeds to be protected against fungal attack, with an effective amount of at least one compound of the formula I, or an N-oxide, or an agriculturally acceptable salt thereof; and to agrochemical compositions comprising at least one compound of the formula I; and to agrochemical compositions further comprising seeds.

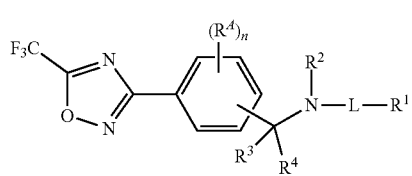

20 Claims, No Drawings

(56) References Cited

FOREIGN PATENT DOCUMENTS

| WO | WO-2017/211649 A1 | 12/2017 |
|----|-------------------|---------|
| WO | WO-2017/211650 A1 | 12/2017 |
| WO | WO-2017/211652 A1 | 12/2017 |
| WO | WO-2017/213252 A1 | 12/2017 |
| WO | WO-2018/011112 A1 | 1/2018 |
| WO | WO-2018/041648 A1 | 3/2018 |
| WO | WO-2018/054711 A1 | 3/2018 |
| WO | WO-2018/054721 A1 | 3/2018 |
| WO | WO-2018/054723 A1 | 3/2018 |
| WO | WO-2018/065182 A1 | 4/2018 |
| WO | WO-2018/073110 A1 | 4/2018 |
| WO | WO-2018/114393 A1 | 6/2018 |
| WO | WO 2018/117034 * | 6/2018 |
| WO | WO-2018/134127 A1 | 7/2018 |
| WO | WO-2018/149754 A1 | 8/2018 |
| WO | WO-2018/153730 A1 | 8/2018 |

OTHER PUBLICATIONS

Machine translation of JP 2020-23442 (Feb. 2020).*
Derwent abstract 2018-50967K, abstracting WO 2018/117034 (Jun. 2018).*
European Search Report for EP Patent Application No. 17157051.8, dated Jun. 12, 2017, 3 pages.
International Search Report and Written Opinion for PCT Patent Application No. PCT/EP2018/053553, dated Apr. 5, 2018.

* cited by examiner

SUBSTITUTED OXADIAZOLES FOR COMBATING PHYTOPATHOGENIC FUNGI

This application is a National Stage application of International Application No. PCT/EP2018/053553, filed Feb. 13, 2018. This application also claims priority under 35 U.S.C. § 119 to European Patent Application No. 17157051.8, filed Feb. 21, 2017.

The present invention relates to novel trifluoromethyloxadiazoles of the formula I, or the N-oxides, or the agriculturally useful salts thereof; and to their use for controlling phytopathogenic fungi; and to a method for combating phytopathogenic harmful fungi, which process comprises treating the fungi, the plants, the soil or seeds to be protected against fungal attack, with an effective amount of at least one compound of the formula I, or an N-oxide, or an agriculturally acceptable salt thereof; and to agrochemical compositions comprising at least one compound of the formula I; and to agrochemical compositions further comprising seeds.

EP 276432 A2 relates to 3-phenyl-5-trifluoromethyloxadiazole derivatives and to their use to combat phytopathogenic microorganisms. WO 2015/185485 A1 describes similar derivatives of trifluoromethyloxadiazoles and their use to combat phytopathogenic microorganisms.

WO 97/30047 A1 describes certain trifluoromethyloxadiazole analogues with fungicidal activity.

WO 2017/213252 A1 discloses further oxadiazole compounds and their use as pesticides.

In many cases, in particular at low application rates, the fungicidal activity of known fungicidal compounds is unsatisfactory. Based on this, it was an objective of the present invention to provide compounds having improved activity and/or a broader activity spectrum against phytopathogenic fungi. This objective is achieved by the oxadiazoles of the formula I and/or their agriculturally useful salts for controlling phytopathogenic fungi.

The compounds described herein differ from compounds known in the prior art in the constitution of the group $-CR^3R^4-NR^2-L-R^1$.

Accordingly, the present invention relates to compounds of the formula I, or the N-oxides, or the agriculturally acceptable salts thereof

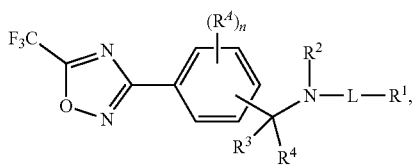

wherein:
$R^4$ is independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
n is 0, 1 or 2;
L is $-(C=S)-$ or $-S(=O)_p-$;
p is 0, 1 or 2;
$R^1$ is $C_1$-$C_6$-alkyl or $C_1$-$C_6$-alkoxy; wherein any of the aliphatic groups are unsubstituted or substituted with 1, 2, 3, 4, 5 or up to the maximum possible number of identical or different radicals selected from the group consisting of hydroxy, cyano, $C_1$-$C_6$-alkyl, $C_1$-$C_6$-alkoxy and $C_3$-$C_8$-cycloalkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_8$-cycloalkyl, $C_3$-$C_8$-cycloalkenyl, $C_3$-$C_8$-cycloalkyl-$C_1$-$C_4$-alkyl, phenyl-$C_1$-$C_4$-alkyl, phenyl, $C(=O)-(C_1$-$C_6$-alkyl) or $C(=O)-(C_1$-$C_6$-alkoxy);
and wherein any of the aliphatic or cyclic groups are unsubstituted or substituted with 1, 2, 3 or up to the maximum possible number of identical or different radicals selected from the group consisting of halogen, hydroxy, cyano, $C_1$-$C_6$-alkyl, $C_1$-$C_6$-alkoxy and $C_3$-$C_8$-cycloalkyl;
$R^3$, $R^4$ independently of each other are selected from the group consisting of hydrogen, halogen, cyano, $C_1$-$C_4$-alkyl, $C_1$-$C_4$-alkenyl, $C_1$-$C_4$-alkynyl, $C_1$-$C_4$-haloalkyl and $C_1$-$C_4$-alkoxy;
or $R^3$ and $R^4$ together with the carbon atom to which they are bound form a saturated 3- to 7-membered carbocycle or a saturated 3- to 6-membered heterocycle; wherein the saturated heterocycle includes beside carbon atoms 1, 2 or 3 heteroatoms independently selected from the group consisting of N, O and S as ring member atoms; and wherein said N ring member atom is substituted with the group $R^N$; wherein
$R^N$ is hydrogen, $C_1$-$C_6$-alkyl or halogen;
and wherein said S ring member atom is unsubstituted or substituted with 1 or 2 oxo radicals; and wherein one or two $CH_2$ groups of the saturated carbocycle or of the saturated heterocycle may be replaced by one or two groups independently selected from $-C(=O)-$ and $-C(=S)-$; and wherein the carbon ring member atoms of the saturated carbocycle or of the saturated heterocycle are unsubstituted or substituted with a total number of 1, 2, 3, 4 or up to the maximum possible number of identical or different radicals selected from the group consisting of halogen, cyano, $C_1$-$C_6$-alkyl, $C_1$-$C_6$-alkoxy and $C_3$-$C_8$-cycloalkyl;
with the exception of compounds of the formula I wherein $R^3$ and $R^4$ both are hydrogen.

Agriculturally acceptable salts of the compounds of the formula I encompass especially the salts of those cations or the acid addition salts of those acids whose cations and anions, respectively, have no adverse effect on the fungicidal action of the compounds 1. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may be substituted with one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of acceptable acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydrobromic acid, sulfuric acid, phosphoric acid or nitric acid.

Compounds of the formula I can exist as one or more stereoisomers. The various stereoisomers include enantiomers, diastereomers, atropisomers arising from restricted rotation about a single bond of asymmetric groups and geometric isomers. They also form part of the subject matter of the present invention. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, e.g. a racemate, individual stereoisomers, or as an optically active form.

Compounds of the formula I can be present in different crystal modifications whose biological activity may differ. They also form part of the subject matter of the present invention.

In respect of the variables, the embodiments of the intermediates obtained during preparation of compounds I correspond to the embodiments of the compounds of formula I. The term "compounds I" refers to compounds of formula I.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "phenyl-$C_1$-$C_4$-alkyl" refers to alkyl having 1 to 4 carbon atoms (as defined above), wherein one hydrogen atom of the alkyl radical is replaced by a phenyl radical.

The term "$C_3$-$C_6$-cycloalkyl" refers to monocyclic saturated hydrocarbon radicals having 3 to 8 carbon ring members such as cyclopropyl ($C_3H_5$), cyclobutyl, cyclopentyl, cyclohexyl, cycloheptyl or cyclooctyl.

The terms "C(=O)—($C_1$-$C_4$-alkyl) or C(=O)—($C_1$-$C_4$-alkoxy)" refer to a radical which is attached through the carbon atom of the —C(=O)— group as indicated by the number valence of the carbon atom.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with . . . " refers to aliphatic groups, cyclic groups and groups, which contain an aliphatic and a cyclic moiety in one group, such as in, for example, $C_3$-$C_8$-cycloalkyl-$C_1$-$C_4$-alkyl; therefore a group which contains an aliphatic moiety and a cyclic moiety both of these moieties may be substituted or unsubstituted independently of each other.

The term "phenyl" refers to an aromatic ring systems including six carbon atoms (commonly referred to as benzene ring.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "saturated 3- to 6-membered heterocycle, wherein the saturated heterocycle includes besides carbon atoms further 1, 2 or 3 heteroatoms selected from N, O and S as ring member atoms", is to be understood as meaning monocyclic heterocycles, for example: a 3- or 4-membered saturated heterocycle which contains 1 or 2 heteroatoms from the group consisting of N, O and S as ring members, such as oxirane, aziridine, thiirane, oxetane, azetidine, thietane, [1,2]dioxetane, [1,2]dithietane, [1,2]diazetidine;

and a 5-membered saturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl.

In respect of the variables, the embodiments of the intermediates correspond to the embodiments of the compounds I. Preference is given to those compounds I and, where applicable, also to compounds of all subformulae provided herein, e. g. formulae I.1, I.2, I.1a, I.1b, I.1c, I.A, I.B, I.C, I.D. I.E, I.F, I.G, I.H, I.J and I.K, wherein variables L, p, $R^1$, $R^2$, $R^3$, $R^4$, $R^A$ and n have independently of each other or more preferably in combination (any possible combination of 2 or more substituents as defined herein) the following meanings:

In a preferred embodiment $R^A$ is independently selected from the group consisting of halogen, $C_1$-$C_6$-alkyl or $C_3$-$C_8$-cycloalkyl. In another preferred embodiment $R^A$ is independently selected from the group consisting of halogen, methyl or ethyl. More preferably $R^A$ is independently selected from the group consisting of halogen, in particular $R^A$ is fluorine.

In one aspect of the invention n is 0, 1 or 2, preferably n is 0 or 1. In a particularly preferred aspect n is 0.

In one aspect of the invention $R^1$ is $C_1$-$C_6$-alkyl or $C_1$-$C_6$-alkoxy; and wherein any of the aliphatic groups are unsubstituted or substituted with 1, 2, 3 or up to the maximum possible number of identical or different radicals selected from the group consisting of $C_1$-$C_6$-alkoxy and $C_3$-$C_8$-cycloalkyl.

In one aspect of the invention $R^2$ is hydrogen, $C_1$-$C_6$-alkyl, $C_1$-$C_6$-alkoxy, $C_2$-$C_6$-alkenyl, ethynyl, propargyl, $C_3$-$C_8$-cycloalkyl, $C_3$-$C_8$-cycloalkenyl, $C_3$-$C_8$-cycloalkyl-$C_1$-$C_4$-alkyl or phenyl; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy; more preferably from halogen, in particular the radical is fluorine.

In another aspect $R^2$ is hydrogen, $C_1$-$C_6$-alkyl, $C_2$-$C_6$-alkenyl, propargyl, $C_3$-$C_8$-cycloalkyl, $C_3$-$C_8$-cycloalkenyl, $C_3$-$C_8$-cycloalkyl-$C_1$-$C_4$-alkyl or phenyl; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy; more preferably from halogen, in particular the radical is fluorine.

In a preferred aspect of the invention $R^2$ is hydrogen, $C_1$-$C_6$-alkyl, $C_1$-$C_6$-alkenyl, propargyl, $C_3$-$C_8$-cycloalkyl, $C_3$-$C_8$-cycloalkyl-$C_1$-$C_4$-alkyl or phenyl; and wherein any of the aliphatic or cyclic groups are unsubstituted or substituted with 1, 2, 3, 4 or up to the maximum possible number of identical or different radicals selected from the group consisting of halogen or $C_1$-$C_6$-alkyl, in particular fluorine.

In another aspect $R^2$ is hydrogen, $C_1$-$C_6$-alkyl, $C_2$-$C_6$-alkenyl, propargyl, $C_3$-$C_8$-cycloalkyl or $C_3$-$C_8$-cycloalkyl-$C_1$-$C_4$-alkyl.

In a further aspect $R^2$ is hydrogen, $C_1$-$C_6$-alkyl, $C_2$-$C_6$-alkenyl or propargyl.

In yet another aspect $R^2$ is hydrogen, methyl, ethyl, iso-propyl, cyclopropyl, cyclopropyl-$CH_2$—, allyl, phenyl, 4-F-phenyl or 2-F-phenyl.

In a more preferred aspect of the invention $R^2$ is hydrogen, methyl, ethyl, n-propyl, iso-propyl, cyclopropyl, cyclopropyl-$CH_2$— or allyl.

In a particularly preferred aspect $R^2$ is hydrogen, methy or ethyl.

In a further aspect $R^2$ is hydrogen, $C_1$-$C_6$-alkyl, $C_2$-$C_6$-alkenyl, $C_3$-$C_8$-cycloalkyl or $C_3$-$C_8$-cycloalkyl-$C_1$-$C_4$-alkyl; in particular hydrogen, methyl, ethyl, iso-propyl, cyclopropyl, cyclopropyl-$CH_2$— or allyl; more particularly hydrogen, methyl or ethyl; and $R^1$ is $C_1$-$C_6$-alkyl or $C_1$-$C_6$-alkoxy; and wherein any of the above-mentioned aliphatic or cyclic groups are unsubstituted or substituted with 1, 2, 3 or up to the maximum possible number of identical or different radicals selected from the group consisting of hydroxy, cyano, $C_1$-$C_6$-alkyl and $C_1$-$C_6$-alkoxy.

In yet another embodiment $R^2$ is hydrogen, $C_1$-$C_6$-alkyl, $C_2$-$C_6$-alkenyl or $C_3$-$C_8$-cycloalkyl; in particular hydrogen, methyl, ethyl, iso-propyl, cyclopropyl, cyclopropyl-$CH_2$— or allyl; more particularly hydrogen, methyl or ethyl; and $R^1$ is $C_1$-$C_6$-alkyl or $C_1$-$C_6$-alkoxy; and wherein the aliphatic groups in $R^1$ are unsubstituted or substituted with 1, 2, 3, 4 or up to the maximum possible number of identical or different radicals selected from the group consisting of $C_1$-$C_6$-alkyl and $C_1$-$C_6$-alkoxy.

In a preferred aspect of the invention $R^2$ is hydrogen, $C_1$-$C_6$-alkyl, $C_2$-$C_6$-alkenyl, $C_3$-$C_8$-cycloalkyl or $C_3$-$C_8$-cycloalkyl-$C_1$-$C_4$-alkyl; in particular hydrogen, methyl, ethyl, iso-propyl, cyclopropyl, cyclopropyl-$CH_2$— or allyl; more particularly hydrogen, methyl or ethyl; and $R^1$ is $C_1$-$C_6$-alkyl or $C_1$-$C_6$-alkoxy; and wherein the alkyl group in $R^1$ is substituted with 1, 2, 3, 4, 5 or up to the maximum possible number of identical or different halogen atoms; and wherein the alkyl group is further unsubstituted or substituted with 1, 2, 3 or up to the maximum possible number of identical or different groups selected from the group consisting of $C_1$-$C_6$-alkyl or $C_3$-$C_8$-cycloalkyl.

In a further embodiment $R^2$ is hydrogen, $C_1$-$C_6$-alkyl, $C_1$-$C_6$-alkenyl, $C_3$-$C_8$-cycloalkyl or $C_3$-$C_8$-cycloalkyl-$C_1$-$C_4$-alkyl; preferably hydrogen, methyl, ethyl, iso-propyl, cyclopropyl, cyclopropyl-$CH_2$— or allyl; and $R^1$ is $C_1$-$C_6$-alkyl; and wherein the alkyl group in $R^1$ is further unsubstituted or substituted with 1, 2, 3 or up to the maximum possible number of identical or different groups selected from the group consisting of $C_1$-$C_6$-alkyl or $C_3$-$C_8$-cycloalkyl.

In one embodiment the invention relates to compounds of the formula I, wherein $R^3$ and $R^4$ independently of each other are hydrogen, halogen, $C_1$-$C_6$-alkyl or $C_1$-$C_6$-haloalkyl; with the exception of compounds of the formula I wherein $R^3$ and $R^4$ both are hydrogen.

In another embodiment the invention relates to compounds of the formula I, wherein $R^3$ and $R^4$ independently of each other are hydrogen or $C_1$-$C_4$-alkyl; preferably hydrogen, methyl or ethyl; with the exception of compounds of the formula I wherein $R^3$ and $R^4$ both are hydrogen.

In a further embodiment $R^3$ and $R^4$ are independently of each other hydrogen, fluorine, methyl or trifluoromethyl; with the exception of compounds of the formula I wherein $R^3$ and $R^4$ both are hydrogen.

In another aspect $R^3$ and $R^4$ are both hydrogen.

In a further aspect $R^3$ is hydrogen and $R^4$ is methyl.

In a further aspect $R^3$ is hydrogen and $R^4$ is trifluoromethyl.

In a further aspect $R^3$ is hydrogen and $R^4$ is difluoromethyl.

In a further aspect $R^3$ is hydrogen and $R^4$ is trichloromethyl.

In a further aspect $R^3$ is hydrogen and $R^4$ is dichloromethyl.

In yet another aspect $R^3$ and $R^4$ are both methyl.

In a further aspect $R^3$ and $R^4$ are both fluorine.

In one embodiment $R^3$ and $R^4$ are both trifluoromethyl.

In one embodiment $R^3$ and $R^4$ together with the carbon atom to which they are bound form a vinyl group or a saturated monocyclic 3- to 5-membered saturated heterocycle or saturated carbocycle; and wherein the saturated heterocycle includes beside one or more carbon atoms no heteroatoms or 1 or 2 heteroatoms independently selected from N, O and S as ring member atoms; and wherein the vinyl group, the heterocycle or the carbocycle is unsubstituted or substituted 1, 2, 3, 4 or up to the maximum possible number of identical or different radicals selected from the group consisting of halogen, cyano and $C_1$-$C_2$-alkyl.

In another embodiment $R^3$ and $R^4$ together with the carbon atom to which they are bound form a vinyl group or a 3- or 4-membered carbocylic ring; and wherein the vinyl group or the carbocylic ring is unsubstituted.

In another aspect $R^3$ and $R^4$ together with the carbon atom to which they are bound form a vinyl group or a cyclopropyl group, wherein the vinyl group or the cyclopropyl group is unsubstituted.

In another aspect $R^3$ and $R^4$ together with the carbon atom to which they are bound form a cyclopropyl ring, wherein the cyclopropyl ring is unsubstituted.

In still another embodiment $R^3$ and $R^4$ together with the carbon atom to which they are bound form a saturated 3-membered heterocycle; wherein the heterocycle includes beside two carbon atoms one heteroatom selected from N, O and S as ring member atoms; and wherein the heterocycle is unsubstituted.

In one embodiment the invention relates to compounds of the formula I.1 or to compounds of the formula I.2, or the N-oxides, or the agriculturally acceptable salts thereof

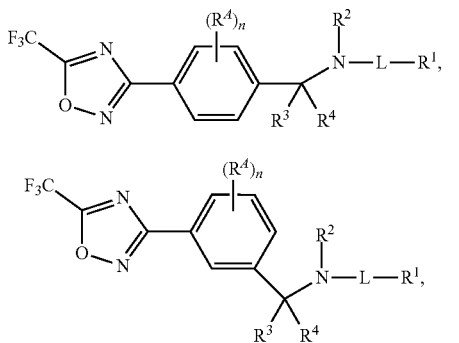

wherein n is 0 or 1, and wherein the meaning of the variables L, $R^A$, $R^1$, $R^2$, $R^3$, $R^4$ are as defined or preferably defined herein for compounds of the formula I.

Another embodiment of the invention relates to compounds of the formulae I.1 or I.2, wherein n is 0; L is —C(=S)—; $R^3$ and $R^4$ are independently selected from hydrogen, halogen, $C_1$-$C_6$-alkyl or $C_1$-$C_6$-haloalkyl; or $R^3$ and $R^4$ together with the carbon atom to which they are bound form a cyclopropyl ring; and wherein $R^1$ and $R^2$ are as defined or preferably defined herein; with the exception of compounds of the formula I wherein $R^3$ and $R^4$ both are hydrogen.

Another embodiment of the invention relates to compounds of the formulae I.1 or I.2, wherein n is 0; L is —SO$_2$—; $R^3$ and $R^4$ are independently selected from hydrogen, halogen, $C_1$-$C_6$-alkyl or $C_1$-$C_6$-haloalkyl; or $R^3$ and $R^4$ together with the carbon atom to which they are bound form a cyclopropyl ring; and wherein $R^1$ and $R^2$ are as defined or preferably defined herein; with the exception of compounds of the formula I wherein $R^3$ and $R^4$ both are hydrogen.

Another embodiment of the invention relates to compounds of the formulae I.1 or I.2, wherein n is 0; L is —C(=S)—; $R^3$ and $R^4$ are independently selected from hydrogen, methyl or trifluoromethyl; and wherein $R^1$ and $R^2$ are as defined or preferably defined herein; with the exception of compounds of the formula I wherein $R^3$ and $R^4$ both are hydrogen.

Another embodiment of the invention relates to compounds of the formulae I.1 or I.2, wherein n is 0; L is —SO$_2$—; $R^3$ and $R^4$ are independently selected from hydrogen, methyl or trifluoromethyl; and wherein $R^1$ and $R^2$ are as defined or preferably defined herein; with the exception of compounds of the formula I wherein $R^3$ and $R^4$ both are hydrogen.

In a further embodiment the invention relates to compounds I.1a of formula I.1, or the N-oxides, or the agriculturally acceptable salts thereof, wherein:

$R^A$ is independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;

n is 0 or 1;

L is —(C=S)— or —S(=O)$_2$—;

$R^1$ is $C_1$-$C_6$-alkyl or $C_1$-$C_6$-alkoxy; and wherein any of the aliphatic groups is unsubstituted or substituted with 1, 2, 3 or up to the maximum possible number of identical or different radicals selected from the group consisting of hydroxy, cyano, $C_1$-$C_6$-alkyl and $C_1$-$C_6$-alkoxy;

$R^2$ is hydrogen, $C_1$-$C_6$-alkyl, $C_2$-$C_6$-alkenyl, propargyl, $C_3$-$C_8$-cycloalkyl or $C_3$-$C_8$-cycloalkyl-$C_1$-$C_4$-alkyl;

$R^3$, $R^4$ independently of each other are hydrogen, halogen, cyano, $C_1$-$C_6$-alkyl or $C_1$-$C_6$-haloalkyl; or $R^3$ and $R^4$ together with the carbon atom to which they are bound form a vinyl group or a saturated monocyclic 3- to 5-membered heterocycle or carbocycle, wherein the heterocycle includes beside carbon atoms 1 or 2 heteroatoms independently selected from N, O and S as ring member atoms; and wherein the vinyl group, the heterocycle or the carbocycle is unsubstituted or substituted with 1, 2, 3, 4 or up to the maximum possible number of identical or different radicals selected from the group consisting of halogen, cyano and $C_1$-$C_2$-alkyl; with the exception of compounds of the formula I wherein $R^3$ and $R^4$ both are hydrogen.

In a further embodiment the invention relates to compounds I.1a, wherein n is 0, and wherein $R^3$ and $R^4$ are independently selected from hydrogen, halogen, $C_1$-$C_6$-alkyl and $C_1$-$C_6$-haloalkyl; or $R^3$ and $R^4$ together with the carbon atom to which they are bound form a cyclopropyl ring; with the exception of compounds of the formula I wherein $R^3$ and $R^4$ both are hydrogen.

In a further embodiment the invention relates to compounds I.1b of formula I.1, or the N-oxides, or the agriculturally acceptable salts thereof, wherein:

$R^A$ is independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;

n is 0 or 1;

L is —(C=S)— or —S(=O)$_2$—;

$R^1$ is $C_1$-$C_6$-alkyl;

$R^2$ is hydrogen, methyl, ethyl, n-propyl, iso-propyl, cyclopropyl, cyclopropyl-CH$_2$— or allyl;

$R^3$, $R^4$ independently of each other are hydrogen, halogen, cyano, $C_1$-$C_6$-alkyl or $C_1$-$C_6$-haloalkyl; or $R^3$ and $R^4$ together with the carbon atom to which they are bound form a vinyl group or a saturated monocyclic 3- to 5-membered heterocycle or carbocycle, wherein the heterocycle includes beside carbon atoms 1 or 2 heteroatoms independently selected from N, O and S as ring member atoms; and wherein the vinyl group, the heterocycle or the carbocycle is unsubstituted or substituted with 1, 2, 3, 4 or up to the maximum possible number of identical or different radicals selected from the group consisting of halogen, cyano and $C_1$-$C_2$-alkyl; with the exception of compounds of the formula I wherein $R^3$ and $R^4$ both are hydrogen.

In a further embodiment the invention relates to compounds I.1b, wherein n is 0, and wherein $R^3$ and $R^4$ are independently selected from hydrogen, halogen, $C_1$-$C_6$-alkyl and $C_1$-$C_6$-haloalkyl; or $R^3$ and $R^4$ together with the carbon atom to which they are bound form a cyclopropyl ring; with the exception of compounds of the formula I wherein $R^3$ and $R^4$ both are hydrogen.

In a further embodiment the invention relates to compounds I.1c of formula I.1, or the N-oxides, or the agriculturally acceptable salts thereof, wherein:

n is 0;

L is —(C=S)— or —S(=O)$_2$—;

$R^1$ is $C_1$-$C_6$-alkyl;

$R^2$ is hydrogen, $C_1$-$C_6$-alkyl, $C_2$-$C_6$-alkenyl, propargyl, $C_3$-$C_8$-cycloalkyl or $C_3$-$C_8$-cycloalkyl-$C_1$-$C_4$-alkyl;

$R^3$, $R^4$ independently of each other are hydrogen, methyl or trifluoromethyl; or $R^3$ and $R^4$ together with the carbon atom to which they are bound form a cyclopropyl ring; with the exception of compounds of the formula I wherein $R^3$ and $R^4$ both are hydrogen.

In a further embodiment the invention relates to compounds I.1c, wherein $R^2$ is hydrogen, methyl, ethyl, n-propyl, iso-propyl, cyclopropyl, cyclopropyl-CH$_2$— or allyl; and wherein $R^3$ and $R^4$ are independently selected from hydrogen, halogen, $C_1$-$C_6$-alkyl and $C_1$-$C_6$-haloalkyl; or $R^3$ and $R^4$ together with the carbon atom to which they are bound form a cyclopropyl ring; with the exception of compounds of the formula I wherein $R^3$ and $R^4$ both are hydrogen.

According to one embodiment, the present invention relates to compounds of the formulae I.A, I.B, I.C, I.D. I.E, I.F, I.G, I.H, I.J and I.K and to their use for controlling phytopathogenic fungi, wherein the variables $R^1$ and $R^2$ in compounds I.A, I.B, I.C, I.D. I.E, I.F, I.G, I.H, I.J and I.K are as defined or preferably defined herein.

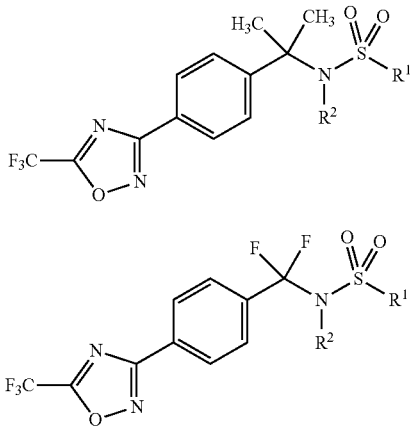

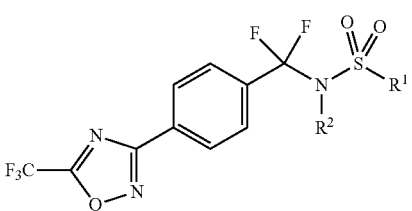

Preference is given to compounds of the formula I, which are compiled in Tables 1 to 10 below, and which may be used according to the invention.

Table 1: Compounds of the formula I.A, in which $R^1$ and $R^2$ for each individual compound corresponds in each case to one line A-1 to A-593 of Table A (compounds I.A.A-1 to I.A.A-593).

This means, for example, that a compound of formula I.A, wherein $R^1$ is 2,2,2-trifluoroethyl and $R^2$ is hydrogen (corresponding to the definition A-4 in Table A) is named I.A.A-4.

Table 2: Compounds of the formula I.B, in which $R^1$ and $R^2$ for each individual compound corresponds in each case to one line A-1 to A-593 of Table A (compounds I.B.A-1 to I.B.A-593).

This means, for example, that a compound of formula I.B, wherein $R^1$ is trifluoromethyl and $R^2$ is methyl (corresponding to the definition A-18 in Table A) is named I.B.A-18.

Table 3: Compounds of the formula I.C, in which $R^1$ and $R^2$ for each individual compound corresponds in each case to one line A-1 to A-593 of Table A (compounds I.C.A-1 to I.C.A-593) Table 4: Compounds of the formula I.D, in which $R^1$ and $R^2$ for each individual compound corresponds in each case to one line A-1 to A-593 of Table A (compounds I.D.A-1 to I.D.A-593).

Table 5: Compounds of the formula I.E, in which $R^1$ and $R^2$ for each individual compound corresponds in each case to one line A-1 to A-593 of Table A (compounds I.E.A-1 to I.E.A-593).

Table 6: Compounds of the formula I.F, in which $R^1$ and $R^2$ for each individual compound corresponds in each case to one line A-1 to A-593 of Table A (compounds I.F.A-1 to I.F.A-593).

Table 7: Compounds of the formula I.G, in which $R^1$ and $R^2$ for each individual compound corresponds in each case to one line A-1 to A-593 of Table A (compounds I.G.A-1 to I.G.A-593).

Table 8: Compounds of the formula I.H, in which $R^1$ and $R^2$ for each individual compound corresponds in each case to one line A-1 to A-593 of Table A (compounds I.H.A-1 to I.H.A-593)

Table 9: Compounds of the formula I.J, in which $R^1$ and $R^2$ for each individual compound corresponds in each case to one line A-1 to A-593 of Table A (compounds I.J.A-1 to I.J.A-593).

Table 10: Compounds of the formula I.K, in which $R^1$ and $R^2$ for each individual compound corresponds in each case to one line A-1 to A-593 of Table A (compounds I.K.A-1 to I.K.A-593).

TABLE A

| No. | $R^1$ | $R^2$ |
|---|---|---|
| A-1 | $CH_3$ | hydrogen |
| A-2 | $CH_2CH_3$ | hydrogen |
| A-3 | $CH_2CH_2CH_3$ | hydrogen |
| A-4 | $CH(CH_3)_2$ | hydrogen |
| A-5 | $CH_2CH_2CH_2CH_3$ | hydrogen |
| A-6 | $CH(CH_3)CH_2CH_3$ | hydrogen |
| A-7 | $CH_2CH(CH_3)CH_3$ | hydrogen |
| A-8 | $CH(CH_2CH_3)_2$ | hydrogen |
| A-9 | $C(CH_3)_3$ | hydrogen |
| A-10 | $OCH_3$ | hydrogen |
| A-11 | $OCH_2CH_3$ | hydrogen |
| A-12 | $OCH_2CH_2CH_3$ | hydrogen |
| A-13 | $OCH(CH_3)_2$ | hydrogen |
| A-14 | $OCH_2CH_2CH_2CH_3$ | hydrogen |
| A-15 | $OCH(CH_3)CH_2CH_3$ | hydrogen |
| A-16 | $OCH_2CH(CH_3)CH_3$ | hydrogen |
| A-17 | $OC(CH_3)_3$ | hydrogen |
| A-18 | difluoromethyl | hydrogen |
| A-19 | trifluoromethyl | hydrogen |
| A-20 | 2,2-difluoroethyl | hydrogen |
| A-21 | 2,2,2-trifluoroethyl | hydrogen |
| A-22 | 2-chloro-2-fluoroethyl | hydrogen |
| A-23 | 2-chloro-2,2-difluoroethyl | hydrogen |
| A-24 | 2,2,2-trichloroethyl | hydrogen |
| A-25 | pentafluoroethyl | hydrogen |
| A-26 | 3,3,3-trifluoropropyl | hydrogen |
| A-27 | $CH_2CF_2CF_3$ | hydrogen |
| A-28 | $CF_2CF_2CF_3$ | hydrogen |
| A-29 | $CH(CH_3)CF_3$ | hydrogen |
| A-30 | $CH_2CF_2CH_3$ | hydrogen |
| A-31 | $CH_2C(CH_3)_2F$ | hydrogen |
| A-32 | $CH_2CH(CH_3)CF_3$ | hydrogen |
| A-33 | $CH_2C(CH_3)_2CF_3$ | hydrogen |
| A-34 | $CH_3$ | methyl |
| A-35 | $CH_2CH_3$ | methyl |
| A-36 | $CH_2CH_2CH_3$ | methyl |
| A-37 | $CH(CH_3)_2$ | methyl |
| A-38 | $CH(CH_2CH_3)_2$ | methyl |
| A-39 | $CH_2CH_2CH_2CH_3$ | methyl |
| A-40 | $CH(CH_3)CH_2CH_3$ | methyl |
| A-41 | $CH_2CH(CH_3)CH_3$ | methyl |
| A-42 | $C(CH_3)_3$ | methyl |
| A-43 | $OCH_3$ | methyl |
| A-44 | $OCH_2CH_3$ | methyl |
| A-45 | $OCH_2CH_2CH_3$ | methyl |
| A-46 | $OCH(CH_3)_2$ | methyl |
| A-47 | $OCH_2CH_2CH_2CH_3$ | methyl |
| A-48 | $OCH(CH_3)CH_2CH_3$ | methyl |
| A-49 | $OCH_2CH(CH_3)CH_3$ | methyl |
| A-50 | $OC(CH_3)_3$ | methyl |
| A-51 | difluoromethyl | methyl |
| A-52 | trifluoromethyl | methyl |
| A-53 | 2,2-difluoroethyl | methyl |
| A-54 | 2,2,2-trifluoroethyl | methyl |
| A-55 | 2-chloro-2-fluoroethyl | methyl |
| A-56 | 2-chloro-2,2-difluoroethyl | methyl |
| A-57 | 2,2,2-trichloroethyl | methyl |
| A-58 | pentafluoroethyl | methyl |
| A-59 | 3,3,3-trifluoropropyl | methyl |
| A-60 | $CH_2CF_2CF_3$ | methyl |
| A-61 | $CF_2CF_2CF_3$ | methyl |
| A-62 | $CH(CH_3)CF_3$ | methyl |
| A-63 | $CH_2CF_2CH_3$ | methyl |
| A-64 | $CH_2C(CH_3)_2F$ | methyl |
| A-65 | $CH_2CH(CH_3)CF_3$ | methyl |
| A-66 | $CH_2C(CH_3)_2CF_3$ | methyl |
| A-67 | $CH_3$ | ethyl |
| A-68 | $CH_2CH_3$ | ethyl |
| A-69 | $CH_2CH_2CH_3$ | ethyl |
| A-70 | $CH(CH_3)_2$ | ethyl |
| A-71 | $CH_2CH_2CH_2CH_3$ | ethyl |
| A-72 | $CH(CH_3)CH_2CH_3$ | ethyl |

TABLE A-continued

| No. | R¹ | R² |
|---|---|---|
| A-73 | CH₂CH(CH₃)CH₃ | ethyl |
| A-74 | CH(CH₂CH₃)₂ | ethyl |
| A-75 | C(CH₃)₃ | ethyl |
| A-76 | OCH₃ | ethyl |
| A-77 | OCH₂CH₃ | ethyl |
| A-78 | OCH₂CH₂CH₃ | ethyl |
| A-79 | OCH(CH₃)₂ | ethyl |
| A-80 | OCH₂CH₂CH₂CH₃ | ethyl |
| A-81 | OCH(CH₃)CH₂CH₃ | ethyl |
| A-82 | OCH₂CH(CH₃)CH₃ | ethyl |
| A-83 | OC(CH₃)₃ | ethyl |
| A-84 | difluoromethyl | ethyl |
| A-85 | trifluoromethyl | ethyl |
| A-86 | 2,2-difluoroethyl | ethyl |
| A-87 | 2,2,2-trifluoroethyl | ethyl |
| A-88 | 2-chloro-2-fluoroethyl | ethyl |
| A-89 | 2-chloro-2,2-difluoroethyl | ethyl |
| A-90 | 2,2,2-trichloroethyl | ethyl |
| A-91 | pentafluoroethyl | ethyl |
| A-92 | 3,3,3-trifluoropropyl | ethyl |
| A-93 | CH₂CF₂CF₃ | ethyl |
| A-94 | CF₂CF₂CF₃ | ethyl |
| A-95 | CH(CH₃)CF₃ | ethyl |
| A-96 | CH₂CF₂CH₃ | ethyl |
| A-97 | CH₂C(CH₃)₂F | ethyl |
| A-98 | CH₂CH(CH₃)CF₃ | ethyl |
| A-99 | CH₂C(CH₃)₂CF₃ | ethyl |
| A-100 | CH₃ | n-propyl |
| A-101 | CH₂CH₃ | n-propyl |
| A-102 | CH₂CH₂CH₃ | n-propyl |
| A-103 | CH(CH₃)₂ | n-propyl |
| A-104 | CH₂CH₂CH₂CH₃ | n-propyl |
| A-105 | CH(CH₃)CH₂CH₃ | n-propyl |
| A-106 | CH₂CH(CH₃)CH₃ | n-propyl |
| A-107 | CH(CH₂CH₃)₂ | n-propyl |
| A-108 | C(CH₃)₃ | n-propyl |
| A-109 | OCH₃ | n-propyl |
| A-110 | OCH₂CH₃ | n-propyl |
| A-111 | OCH₂CH₂CH₃ | n-propyl |
| A-112 | OCH(CH₃)₂ | n-propyl |
| A-113 | OCH₂CH₂CH₂CH₃ | n-propyl |
| A-114 | OCH(CH₃)CH₂CH₃ | n-propyl |
| A-115 | OCH₂CH(CH₃)CH₃ | n-propyl |
| A-116 | OC(CH₃)₃ | n-propyl |
| A-117 | difluoromethyl | n-propyl |
| A-118 | trifluoromethyl | n-propyl |
| A-119 | 2,2-difluoroethyl | n-propyl |
| A-120 | 2,2,2-trifluoroethyl | n-propyl |
| A-121 | 2-chloro-2-fluoroethyl | n-propyl |
| A-122 | 2-chloro-2,2-difluoroethyl | n-propyl |
| A-123 | 2,2,2-trichloroethyl | n-propyl |
| A-124 | pentafluoroethyl | n-propyl |
| A-125 | 3,3,3-trifluoropropyl | n-propyl |
| A-126 | CH₂CF₂CF₃ | n-propyl |
| A-127 | CF₂CF₂CF₃ | n-propyl |
| A-128 | CH(CH₃)CF₃ | n-propyl |
| A-129 | CH₂CF₂CH₃ | n-propyl |
| A-130 | CH₂C(CH₃)₂F | n-propyl |
| A-131 | CH₂CH(CH₃)CF₃ | n-propyl |
| A-132 | CH₂C(CH₃)₂CF₃ | n-propyl |
| A-133 | CH₃ | vinyl |
| A-134 | CH₂CH₃ | vinyl |
| A-135 | CH₂CH₂CH₃ | vinyl |
| A-136 | CH(CH₃)₂ | vinyl |
| A-137 | CH₂CH₂CH₂CH₃ | vinyl |
| A-138 | CH(CH₃)CH₂CH₃ | vinyl |
| A-139 | CH₂CH(CH₃)CH₃ | vinyl |
| A-140 | C(CH₃)₃ | vinyl |
| A-141 | CH(CH₂CH₃)₂ | vinyl |
| A-142 | OCH₃ | vinyl |
| A-143 | OCH₂CH₃ | vinyl |
| A-144 | OCH₂CH₂CH₃ | vinyl |
| A-145 | OCH(CH₃)₂ | vinyl |
| A-146 | OCH₂CH₂CH₂CH₃ | vinyl |
| A-147 | OCH(CH₃)CH₂CH₃ | vinyl |
| A-148 | OCH₂CH(CH₃)CH₃ | vinyl |
| A-149 | OC(CH₃)₃ | vinyl |
| A-150 | difluoromethyl | vinyl |
| A-151 | trifluoromethyl | vinyl |
| A-152 | 2,2-difluoroethyl | vinyl |
| A-153 | 2,2,2-trifluoroethyl | vinyl |
| A-154 | 2-chloro-2-fluoroethyl | vinyl |
| A-155 | 2-chloro-2,2-difluoroethyl | vinyl |
| A-156 | 2,2,2-trichloroethyl | vinyl |
| A-157 | pentafluoroethyl | vinyl |
| A-158 | 3,3,3-trifluoropropyl | vinyl |
| A-159 | CH₂CF₂CF₃ | vinyl |
| A-160 | CF₂CF₂CF₃ | vinyl |
| A-161 | CH(CH₃)CF₃ | vinyl |
| A-162 | CH₂CF₂CH₃ | vinyl |
| A-163 | CH₂C(CH₃)₂F | vinyl |
| A-164 | CH₂CH(CH₃)CF₃ | vinyl |
| A-165 | CH₂C(CH₃)₂CF₃ | vinyl |
| A-166 | CH₃ | tert-butyl |
| A-167 | CH₂CH₃ | tert-butyl |
| A-168 | CH₂CH₂CH₃ | tert-butyl |
| A-169 | CH(CH₃)₂ | tert-butyl |
| A-170 | CH₂CH₂CH₂CH₃ | tert-butyl |
| A-171 | CH(CH₃)CH₂CH₃ | tert-butyl |
| A-172 | CH₂CH(CH₃)CH₃ | tert-butyl |
| A-173 | CH(CH₂CH₃)₂ | tert-butyl |
| A-174 | C(CH₃)₃ | tert-butyl |
| A-175 | OCH₃ | tert-butyl |
| A-176 | OCH₂CH₃ | tert-butyl |
| A-177 | OCH₂CH₂CH₃ | tert-butyl |
| A-178 | OCH(CH₃)₂ | tert-butyl |
| A-179 | OCH₂CH₂CH₂CH₃ | tert-butyl |
| A-180 | OCH(CH₃)CH₂CH₃ | tert-butyl |
| A-181 | OCH₂CH(CH₃)CH₃ | tert-butyl |
| A-182 | OC(CH₃)₃ | tert-butyl |
| A-183 | difluoromethyl | tert-butyl |
| A-184 | trifluoromethyl | tert-butyl |
| A-185 | 2,2-difluoroethyl | tert-butyl |
| A-186 | 2,2,2-trifluoroethyl | tert-butyl |
| A-187 | 2-chloro-2-fluoroethyl | tert-butyl |
| A-188 | 2-chloro-2,2-difluoroethyl | tert-butyl |
| A-189 | 2,2,2-trichloroethyl | tert-butyl |
| A-190 | pentafluoroethyl | tert-butyl |
| A-191 | 3,3,3-trifluoropropyl | tert-butyl |
| A-192 | CH₂CF₂CF₃ | tert-butyl |
| A-193 | CF₂CF₂CF₃ | tert-butyl |
| A-194 | CH(CH₃)CF₃ | tert-butyl |
| A-195 | CH₂CF₂CH₃ | tert-butyl |
| A-196 | CH₂C(CH₃)₂F | tert-butyl |
| A-197 | CH₂CH(CH₃)CF₃ | tert-butyl |
| A-198 | CH₂C(CH₃)₂CF₃ | tert-butyl |
| A-199 | CH₃ | iso-propyl |
| A-200 | CH₂CH₃ | iso-propyl |
| A-201 | CH₂CH₂CH₃ | iso-propyl |
| A-202 | CH(CH₃)₂ | iso-propyl |
| A-203 | CH₂CH₂CH₂CH₃ | iso-propyl |
| A-204 | CH(CH₃)CH₂CH₃ | iso-propyl |
| A-205 | CH₂CH(CH₃)CH₃ | iso-propyl |
| A-206 | CH(CH₂CH₃)₂ | iso-propyl |
| A-207 | C(CH₃)₃ | iso-propyl |
| A-208 | OCH₃ | iso-propyl |
| A-209 | OCH₂CH₃ | iso-propyl |
| A-210 | OCH₂CH₂CH₃ | iso-propyl |
| A-211 | OCH(CH₃)₂ | iso-propyl |
| A-212 | OCH₂CH₂CH₂CH₃ | iso-propyl |
| A-213 | OCH(CH₃)CH₂CH₃ | iso-propyl |
| A-214 | OCH₂CH(CH₃)CH₃ | iso-propyl |
| A-215 | OC(CH₃)₃ | iso-propyl |
| A-216 | difluoromethyl | iso-propyl |

TABLE A-continued

| No. | R¹ | R² |
|---|---|---|
| A-217 | trifluoromethyl | iso-propyl |
| A-218 | 2,2-difluoroethyl | iso-propyl |
| A-219 | 2,2,2-trifluoroethyl | iso-propyl |
| A-220 | 2-chloro-2-fluoroethyl | iso-propyl |
| A-221 | 2-chloro-2,2-difluoroethyl | iso-propyl |
| A-222 | 2,2,2-trichloroethyl | iso-propyl |
| A-223 | pentafluoroethyl | iso-propyl |
| A-224 | 3,3,3-trifluoropropyl | iso-propyl |
| A-225 | $CH_2CF_2CF_3$ | iso-propyl |
| A-226 | $CF_2CF_2CF_3$ | iso-propyl |
| A-227 | $CH(CH_3)CF_3$ | iso-propyl |
| A-228 | $CH_2CF_2CH_3$ | iso-propyl |
| A-229 | $CH_2C(CH_3)_2F$ | iso-propyl |
| A-230 | $CH_2CH(CH_3)CF_3$ | iso-propyl |
| A-231 | $CH_2C(CH_3)_2CF_3$ | iso-propyl |
| A-232 | $CH_3$ | cyclopropyl |
| A-233 | $CH_2CH_3$ | cyclopropyl |
| A-234 | $CH_2CH_2CH_3$ | cyclopropyl |
| A-235 | $CH(CH_3)_2$ | cyclopropyl |
| A-236 | $CH_2CH_2CH_2CH_3$ | cyclopropyl |
| A-237 | $CH(CH_3)CH_2CH_3$ | cyclopropyl |
| A-238 | $CH_2CH(CH_3)CH_3$ | cyclopropyl |
| A-239 | $CH(CH_2CH_3)_2$ | cyclopropyl |
| A-240 | $C(CH_3)_3$ | cyclopropyl |
| A-241 | $OCH_3$ | cyclopropyl |
| A-242 | $OCH_2CH_3$ | cyclopropyl |
| A-243 | $OCH_2CH_2CH_3$ | cyclopropyl |
| A-244 | $OCH(CH_3)_2$ | cyclopropyl |
| A-245 | $OCH_2CH_2CH_2CH_3$ | cyclopropyl |
| A-246 | $OCH(CH_3)CH_2CH_3$ | cyclopropyl |
| A-247 | $OCH_2CH(CH_3)CH_3$ | cyclopropyl |
| A-248 | $OC(CH_3)_3$ | cyclopropyl |
| A-249 | difluoromethyl | cyclopropyl |
| A-250 | trifluoromethyl | cyclopropyl |
| A-251 | 2,2-difluoroethyl | cyclopropyl |
| A-252 | 2,2,2-trifluoroethyl | cyclopropyl |
| A-253 | 2-chloro-2-fluoroethyl | cyclopropyl |
| A-254 | 2-chloro-2,2-difluoroethyl | cyclopropyl |
| A-255 | 2,2,2-trichloroethyl | cyclopropyl |
| A-256 | pentafluoroethyl | cyclopropyl |
| A-257 | 3,3,3-trifluoropropyl | cyclopropyl |
| A-258 | $CH_2CF_2CF_3$ | cyclopropyl |
| A-259 | $CF_2CF_2CF_3$ | cyclopropyl |
| A-260 | $CH(CH_3)CF_3$ | cyclopropyl |
| A-261 | $CH_2CF_2CH_3$ | cyclopropyl |
| A-262 | $CH_2C(CH_3)_2F$ | cyclopropyl |
| A-263 | $CH_2CH(CH_3)CF_3$ | cyclopropyl |
| A-264 | $CH_2C(CH_3)_2CF_3$ | cyclopropyl |
| A-265 | $CH_3$ | cyclobutyl |
| A-266 | $CH_2CH_3$ | cyclobutyl |
| A-267 | $CH_2CH_2CH_3$ | cyclobutyl |
| A-268 | $CH(CH_3)_2$ | cyclobutyl |
| A-269 | $CH_2CH_2CH_2CH_3$ | cyclobutyl |
| A-270 | $CH(CH_3)CH_2CH_3$ | cyclobutyl |
| A-271 | $CH_2CH(CH_3)CH_3$ | cyclobutyl |
| A-272 | $CH(CH_2CH_3)_2$ | cyclobutyl |
| A-273 | $C(CH_3)_3$ | cyclobutyl |
| A-274 | $OCH_3$ | cyclobutyl |
| A-275 | $OCH_2CH_3$ | cyclobutyl |
| A-276 | $OCH_2CH_2CH_3$ | cyclobutyl |
| A-277 | $OCH(CH_3)_2$ | cyclobutyl |
| A-278 | $OCH_2CH_2CH_2CH_3$ | cyclobutyl |
| A-279 | $OCH(CH_3)CH_2CH_3$ | cyclobutyl |
| A-280 | $OCH_2CH(CH_3)CH_3$ | cyclobutyl |
| A-281 | $OC(CH_3)_3$ | cyclobutyl |
| A-282 | difluoromethyl | cyclobutyl |
| A-283 | trifluoromethyl | cyclobutyl |
| A-284 | 2,2-difluoroethyl | cyclobutyl |
| A-285 | 2,2,2-trifluoroethyl | cyclobutyl |
| A-286 | 2-chloro-2-fluoroethyl | cyclobutyl |
| A-287 | 2-chloro-2,2-difluoroethyl | cyclobutyl |
| A-288 | 2,2,2-trichloroethyl | cyclobutyl |
| A-289 | pentafluoroethyl | cyclobutyl |
| A-290 | 3,3,3-trifluoropropyl | cyclobutyl |
| A-291 | $CH_2CF_2CF_3$ | cyclobutyl |
| A-292 | $CF_2CF_2CF_3$ | cyclobutyl |
| A-293 | $CH(CH_3)CF_3$ | cyclobutyl |
| A-294 | $CH_2CF_2CH_3$ | cyclobutyl |
| A-295 | $CH_2C(CH_3)_2F$ | cyclobutyl |
| A-296 | $CH_2CH(CH_3)CF_3$ | cyclobutyl |
| A-297 | $CH_2C(CH_3)_2CF_3$ | cyclobutyl |
| A-298 | $CH_3$ | cyclopentyl |
| A-299 | $CH_2CH_3$ | cyclopentyl |
| A-300 | $CH_2CH_2CH_3$ | cyclopentyl |
| A-301 | $CH(CH_3)_2$ | cyclopentyl |
| A-302 | $CH_2CH_2CH_2CH_3$ | cyclopentyl |
| A-303 | $CH(CH_3)CH_2CH_3$ | cyclopentyl |
| A-304 | $CH_2CH(CH_3)CH_3$ | cyclopentyl |
| A-305 | $CH(CH_2CH_3)_2$ | cyclopentyl |
| A-306 | $C(CH_3)_3$ | cyclopentyl |
| A-307 | $OCH_3$ | cyclopentyl |
| A-308 | $OCH_2CH_3$ | cyclopentyl |
| A-309 | $OCH_2CH_2CH_3$ | cyclopentyl |
| A-310 | $OCH(CH_3)_2$ | cyclopentyl |
| A-311 | $OCH_2CH_2CH_2CH_3$ | cyclopentyl |
| A-312 | $OCH(CH_3)CH_2CH_3$ | cyclopentyl |
| A-313 | $OCH_2CH(CH_3)CH_3$ | cyclopentyl |
| A-314 | $OC(CH_3)_3$ | cyclopentyl |
| A-315 | difluoromethyl | cyclopentyl |
| A-316 | trifluoromethyl | cyclopentyl |
| A-317 | 2,2-difluoroethyl | cyclopentyl |
| A-318 | 2,2,2-trifluoroethyl | cyclopentyl |
| A-319 | 2-chloro-2-fluoroethyl | cyclopentyl |
| A-320 | 2-chloro-2,2-difluoroethyl | cyclopentyl |
| A-321 | 2,2,2-trichloroethyl | cyclopentyl |
| A-322 | pentafluoroethyl | cyclopentyl |
| A-323 | 3,3,3-trifluoropropyl | cyclopentyl |
| A-324 | $CH_2CF_2CF_3$ | cyclobutyl |
| A-325 | $CF_2CF_2CF_3$ | cyclopentyl |
| A-326 | $CH(CH_3)CF_3$ | cyclopentyl |
| A-327 | $CH_2CF_2CH_3$ | cyclopentyl |
| A-328 | $CH_2C(CH_3)_2F$ | cyclopentyl |
| A-329 | $CH_2CH(CH_3)CF_3$ | cyclopentyl |
| A-330 | $CH_2C(CH_3)_2CF_3$ | cyclopentyl |
| A-331 | $CH_3$ | cyclohexyl |
| A-332 | $CH_2CH_3$ | cyclohexyl |
| A-333 | $CH_2CH_2CH_3$ | cyclohexyl |
| A-334 | $CH(CH_3)_2$ | cyclohexyl |
| A-335 | $CH_2CH_2CH_2CH_3$ | cyclohexyl |
| A-336 | $CH(CH_3)CH_2CH_3$ | cyclohexyl |
| A-337 | $CH_2CH(CH_3)CH_3$ | cyclohexyl |
| A-338 | $CH(CH_2CH_3)_2$ | cyclohexyl |
| A-339 | $C(CH_3)_3$ | cyclohexyl |
| A-340 | $OCH_3$ | cyclohexyl |
| A-341 | $OCH_2CH_3$ | cyclohexyl |
| A-342 | $OCH_2CH_2CH_3$ | cyclohexyl |
| A-343 | $OCH(CH_3)_2$ | cyclohexyl |
| A-344 | $OCH_2CH_2CH_2CH_3$ | cyclohexyl |
| A-345 | $OCH(CH_3)CH_2CH_3$ | cyclohexyl |
| A-346 | $OCH_2CH(CH_3)CH_3$ | cyclohexyl |
| A-347 | $OC(CH_3)_3$ | cyclohexyl |
| A-348 | difluoromethyl | cyclohexyl |
| A-349 | trifluoromethyl | cyclohexyl |
| A-350 | 2,2-difluoroethyl | cyclohexyl |
| A-351 | 2,2,2-trifluoroethyl | cyclohexyl |
| A-352 | 2-chloro-2-fluoroethyl | cyclohexyl |
| A-353 | 2-chloro-2,2-difluoroethyl | cyclohexyl |
| A-354 | 2,2,2-trichloroethyl | cyclohexyl |
| A-355 | pentafluoroethyl | cyclohexyl |
| A-356 | 3,3,3-trifluoropropyl | cyclohexyl |

TABLE A-continued

| No. | R¹ | R² |
|---|---|---|
| A-357 | CH₂CF₂CF₃ | cyclohexyl |
| A-358 | CF₂CF₂CF₃ | cyclohexyl |
| A-359 | CH(CH₃)CF₃ | cyclohexyl |
| A-360 | CH₂CF₂CH₃ | cyclohexyl |
| A-361 | CH₂C(CH₃)₂F | cyclohexyl |
| A-362 | CH₂CH(CH₃)CF₃ | cyclohexyl |
| A-363 | CH₂C(CH₃)₂CF₃ | cyclohexyl |
| A-364 | CH₃ | allyl |
| A-365 | CH₂CH₃ | allyl |
| A-366 | CH₂CH₂CH₃ | allyl |
| A-367 | CH(CH₃)₂ | allyl |
| A-368 | CH₂CH₂CH₂CH₃ | allyl |
| A-369 | CH(CH₃)CH₂CH₃ | allyl |
| A-370 | CH₂CH(CH₃)CH₃ | allyl |
| A-371 | CH(CH₂CH₃)₂ | allyl |
| A-372 | C(CH₃)₃ | allyl |
| A-373 | OCH₃ | allyl |
| A-374 | OCH₂CH₃ | allyl |
| A-375 | OCH₂CH₂CH₃ | allyl |
| A-376 | OCH(CH₃)₂ | allyl |
| A-377 | OCH₂CH₂CH₂CH₃ | allyl |
| A-378 | OCH(CH₃)CH₂CH₃ | allyl |
| A-379 | OCH₂CH(CH₃)CH₃ | allyl |
| A-380 | OC(CH₃)₃ | allyl |
| A-381 | difluoromethyl | allyl |
| A-382 | trifluoromethyl | allyl |
| A-383 | 2,2-difluoroethyl | allyl |
| A-384 | 2,2,2-trifluoroethyl | allyl |
| A-385 | 2-chloro-2-fluoroethyl | allyl |
| A-386 | 2-chloro-2,2-difluoroethyl | allyl |
| A-387 | 2,2,2-trichloroethyl | allyl |
| A-388 | pentafluoroethyl | allyl |
| A-389 | 3,3,3-trifluoropropyl | allyl |
| A-390 | CH₂CF₂CF₃ | allyl |
| A-391 | CF₂CF₂CF₃ | allyl |
| A-392 | CH(CH₃)CF₃ | allyl |
| A-393 | CH₂CF₂CH₃ | allyl |
| A-394 | CH₂C(CH₃)₂F | allyl |
| A-395 | CH₂CH(CH₃)CF₃ | allyl |
| A-396 | CH₂C(CH₃)₂CF₃ | allyl |
| A-397 | CH₃ | phenyl |
| A-398 | CH₂CH₃ | phenyl |
| A-399 | CH₂CH₂CH₃ | phenyl |
| A-400 | CH(CH₃)₂ | phenyl |
| A-401 | CH₂CH₂CH₂CH₃ | phenyl |
| A-402 | CH(CH₃)CH₂CH₃ | phenyl |
| A-403 | CH₂CH(CH₃)CH₃ | phenyl |
| A-404 | CH(CH₂CH₃)₂ | phenyl |
| A-405 | C(CH₃)₃ | phenyl |
| A-406 | OCH₃ | phenyl |
| A-407 | OCH₂CH₃ | phenyl |
| A-408 | OCH₂CH₂CH₃ | phenyl |
| A-409 | OCH(CH₃)₂ | phenyl |
| A-410 | OCH₂CH₂CH₂CH₃ | phenyl |
| A-411 | OCH(CH₃)CH₂CH₃ | phenyl |
| A-412 | OCH₂CH(CH₃)CH₃ | phenyl |
| A-413 | OC(CH₃)₃ | phenyl |
| A-414 | difluoromethyl | phenyl |
| A-415 | trifluoromethyl | phenyl |
| A-416 | 2,2-difluoroethyl | phenyl |
| A-417 | 2,2,2-trifluoroethyl | phenyl |
| A-418 | 2-chloro-2-fluoroethyl | phenyl |
| A-419 | 2-chloro-2,2-difluoroethyl | phenyl |
| A-420 | 2,2,2-trichloroethyl | phenyl |
| A-421 | pentafluoroethyl | phenyl |
| A-422 | 3,3,3-trifluoropropyl | phenyl |
| A-423 | CH₂CF₂CF₃ | phenyl |
| A-424 | CF₂CF₂CF₃ | phenyl |
| A-425 | CH(CH₃)CF₃ | phenyl |
| A-426 | CH₂CF₂CH₃ | phenyl |
| A-427 | CH₂C(CH₃)₂F | phenyl |
| A-428 | CH₂CH(CH₃)CF₃ | phenyl |
| A-429 | CH₂C(CH₃)₂CF₃ | phenyl |
| A-430 | CH₃ | 4-fluoro-phenyl |
| A-431 | CH₂CH₃ | 4-fluoro-phenyl |
| A-432 | CH₂CH₂CH₃ | 4-fluoro-phenyl |
| A-433 | CH(CH₃)₂ | 4-fluoro-phenyl |
| A-434 | CH₂CH₂CH₂CH₃ | 4-fluoro-phenyl |
| A-435 | CH(CH₃)CH₂CH₃ | 4-fluoro-phenyl |
| A-436 | CH₂CH(CH₃)CH₃ | 4-fluoro-phenyl |
| A-437 | CH(CH₂CH₃)₂ | 4-fluoro-phenyl |
| A-438 | C(CH₃)₃ | 4-fluoro-phenyl |
| A-439 | OCH₃ | 4-fluoro-phenyl |
| A-440 | OCH₂CH₃ | 4-fluoro-phenyl |
| A-441 | OCH₂CH₂CH₃ | 4-fluoro-phenyl |
| A-442 | OCH(CH₃)₂ | 4-fluoro-phenyl |
| A-443 | OCH₂CH₂CH₂CH₃ | 4-fluoro-phenyl |
| A-444 | OCH(CH₃)CH₂CH₃ | 4-fluoro-phenyl |
| A-445 | OCH₂CH(CH₃)CH₃ | 4-fluoro-phenyl |
| A-446 | OC(CH₃)₃ | 4-fluoro-phenyl |
| A-447 | difluoromethyl | 4-fluoro-phenyl |
| A-448 | trifluoromethyl | 4-fluoro-phenyl |
| A-449 | 2,2-difluoroethyl | 4-fluoro-phenyl |
| A-450 | 2,2,2-trifluoroethyl | 4-fluoro-phenyl |
| A-451 | 2-chloro-2-fluoroethyl | 4-fluoro-phenyl |
| A-452 | 2-chloro-2,2-difluoroethyl | 4-fluoro-phenyl |
| A-453 | 2,2,2-trichloroethyl | 4-fluoro-phenyl |
| A-454 | pentafluoroethyl | 4-fluoro-phenyl |
| A-455 | 3,3,3-trifluoropropyl | 4-fluoro-phenyl |
| A-456 | CH₂CF₂CF₃ | 4-fluoro-phenyl |
| A-457 | CF₂CF₂CF₃ | 4-fluoro-phenyl |
| A-458 | CH(CH₃)CF₃ | 4-fluoro-phenyl |
| A-459 | CH₂CF₂CH₃ | 4-fluoro-phenyl |
| A-460 | CH₂C(CH₃)₂F | 4-fluoro-phenyl |
| A-461 | CH₂CH(CH₃)CF₃ | 4-fluoro-phenyl |
| A-462 | CH₂C(CH₃)₂CF₃ | 4-fluoro-phenyl |
| A-463 | CH₃ | 2-fluoro-phenyl |
| A-464 | CH₂CH₃ | 2-fluoro-phenyl |
| A-465 | CH₂CH₂CH₃ | 2-fluoro-phenyl |
| A-466 | CH(CH₃)₂ | 2-fluoro-phenyl |
| A-467 | CH₂CH₂CH₂CH₃ | 2-fluoro-phenyl |

TABLE A-continued

| No. | R¹ | R² |
|---|---|---|
| A-468 | CH(CH₃)CH₂CH₃ | 2-fluoro-phenyl |
| A-469 | CH₂CH(CH₃)CH₃ | 2-fluoro-phenyl |
| A-470 | CH(CH₂CH₃)₂ | 2-fluoro-phenyl |
| A-471 | C(CH₃)₃ | 2-fluoro-phenyl |
| A-472 | OCH₃ | 2-fluoro-phenyl |
| A-473 | OCH₂CH₃ | 2-fluoro-phenyl |
| A-474 | OCH₂CH₂CH₃ | 2-fluoro-phenyl |
| A-475 | OCH(CH₃)₂ | 2-fluoro-phenyl |
| A-476 | OCH₂CH₂CH₂CH₃ | 2-fluoro-phenyl |
| A-477 | OCH(CH₃)CH₂CH₃ | 2-fluoro-phenyl |
| A-478 | OCH₂CH(CH₃)CH₃ | 2-fluoro-phenyl |
| A-479 | OC(CH₃)₃ | 2-fluoro-phenyl |
| A-480 | difluoromethyl | 2-fluoro-phenyl |
| A-481 | trifluoromethyl | 2-fluoro-phenyl |
| A-482 | 2,2-difluoroethyl | 2-fluoro-phenyl |
| A-483 | 2,2,2-trifluoroethyl | 2-fluoro-phenyl |
| A-484 | 2-chloro-2-fluoroethyl | 2-fluoro-phenyl |
| A-485 | 2-chloro-2,2-difluoroethyl | 2-fluoro-phenyl |
| A-486 | 2,2,2-trichloroethyl | 2-fluoro-phenyl |
| A-487 | pentafluoroethyl | 2-fluoro-phenyl |
| A-488 | 3,3,3-trifluoropropyl | 2-fluoro-phenyl |
| A-489 | CH₂CF₂CF₃ | 2-fluoro-phenyl |
| A-490 | CF₂CF₂CF₃ | 2-fluoro-phenyl |
| A-491 | CH(CH₃)CF₃ | 2-fluoro-phenyl |
| A-492 | CH₂CF₂CH₃ | 2-fluoro-phenyl |
| A-493 | CH₂C(CH₃)₂F | 2-fluoro-phenyl |
| A-494 | CH₂CH(CH₃)CF₃ | 2-fluoro-phenyl |
| A-495 | CH₂C(CH₃)₂CF₃ | 2-fluoro-phenyl |
| A-496 | CH₃ | 2,4-difluoro-phenyl |
| A-497 | CH₂CH₃ | 2,4-difluoro-phenyl |
| A-498 | CH₂CH₂CH₃ | 2,4-difluoro-phenyl |
| A-499 | CH(CH₃)₂ | 2,4-difluoro-phenyl |
| A-500 | CH₂CH₂CH₂CH₃ | 2,4-difluoro-phenyl |
| A-501 | CH(CH₃)CH₂CH₃ | 2,4-difluoro-phenyl |
| A-502 | CH₂CH(CH₃)CH₃ | 2,4-difluoro-phenyl |
| A-503 | CH(CH₂CH₃)₂ | 2,4-difluoro-phenyl |
| A-504 | C(CH₃)₃ | 2,4-difluoro-phenyl |
| A-505 | OCH₃ | 2,4-difluoro-phenyl |
| A-506 | OCH₂CH₃ | 2,4-difluoro-phenyl |
| A-507 | OCH₂CH₂CH₃ | 2,4-difluoro-phenyl |
| A-508 | OCH(CH₃)₂ | 2,4-difluoro-phenyl |
| A-509 | OCH₂CH₂CH₂CH₃ | 2,4-difluoro-phenyl |
| A-510 | OCH(CH₃)CH₂CH₃ | 2,4-difluoro-phenyl |
| A-511 | OCH₂CH(CH₃)CH₃ | 2,4-difluoro-phenyl |
| A-512 | OC(CH₃)₃ | 2,4-difluoro-phenyl |
| A-513 | difluoromethyl | 2,4-difluoro-phenyl |
| A-514 | trifluoromethyl | 2,4-difluoro-phenyl |
| A-515 | 2,2-difluoroethyl | 2,4-difluoro-phenyl |
| A-516 | 2,2,2-trifluoroethyl | 2,4-difluoro-phenyl |
| A-517 | 2-chloro-2-fluoroethyl | 2,4-difluoro-phenyl |
| A-518 | 2-chloro-2,2-difluoroethyl | 2,4-difluoro-phenyl |
| A-519 | 2,2,2-trichloroethyl | 2,4-difluoro-phenyl |
| A-520 | pentafluoroethyl | 2,4-difluoro-phenyl |
| A-521 | 3,3,3-trifluoropropyl | 2,4-difluoro-phenyl |
| A-522 | CH₂CF₂CF₃ | 2,4-difluoro-phenyl |
| A-523 | CF₂CF₂CF₃ | 2,4-difluoro-phenyl |
| A-524 | CH(CH₃)CF₃ | 2,4-difluoro-phenyl |
| A-525 | CH₂CF₂CH₃ | 2,4-difluoro-phenyl |
| A-526 | CH₂C(CH₃)₂F | 2,4-difluoro-phenyl |
| A-527 | CH₂CH(CH₃)CF₃ | 2,4-difluoro-phenyl |
| A-528 | CH₂C(CH₃)₂CF₃ | 2,4-difluoro-phenyl |
| A-529 | CH₃ | propargyl |
| A-530 | CH₂CH₃ | propargyl |
| A-531 | CH₂CH₂CH₃ | propargyl |
| A-532 | CH(CH₃)₂ | propargyl |
| A-533 | CH₂CH₂CH₂CH₃ | propargyl |
| A-534 | CH(CH₃)CH₂CH₃ | propargyl |
| A-535 | CH₂CH(CH₃)CH₃ | propargyl |
| A-536 | CH(CH₂CH₃)₂ | propargyl |
| A-537 | C(CH₃)₃ | propargyl |
| A-538 | OCH₃ | propargyl |
| A-539 | OCH₂CH₃ | propargyl |
| A-540 | OCH₂CH₂CH₃ | propargyl |
| A-541 | OCH(CH₃)₂ | propargyl |
| A-542 | OCH₂CH₂CH₂CH₃ | propargyl |
| A-543 | OCH(CH₃)CH₂CH₃ | propargyl |
| A-544 | OCH₂CH(CH₃)CH₃ | propargyl |
| A-545 | OC(CH₃)₃ | propargyl |
| A-546 | difluoromethyl | propargyl |
| A-547 | trifluoromethyl | propargyl |
| A-548 | 2,2-difluoroethyl | propargyl |
| A-549 | 2,2,2-trifluoroethyl | propargyl |
| A-550 | 2-chloro-2-fluoroethyl | propargyl |
| A-551 | 2-chloro-2,2-difluoroethyl | propargyl |
| A-552 | 2,2,2-trichloroethyl | propargyl |
| A-553 | pentafluoroethyl | propargyl |
| A-554 | 3,3,3-trifluoropropyl | propargyl |
| A-555 | CH₂CF₂CF₃ | propargyl |
| A-556 | CF₂CF₂CF₃ | propargyl |
| A-557 | CH(CH₃)CF₃ | propargyl |
| A-558 | CH₂CF₂CH₃ | propargyl |
| A-559 | CH₂C(CH₃)₂F | propargyl |
| A-560 | CH₂CH(CH₃)CF₃ | propargyl |
| A-561 | CH₂C(CH₃)₂CF₃ | propargyl |
| A-562 | CH₃ | cyclopropyl-CH2- |

TABLE A-continued

| No. | $R^1$ | $R^2$ |
|---|---|---|
| A-563 | $CH_2CH_3$ | cyclopropyl-$CH_2$- |
| A-564 | $CH_2CH_2CH_3$ | cyclopropyl-$CH_2$- |
| A-565 | $CH(CH_3)_2$ | cyclopropyl-$CH_2$- |
| A-566 | $CH_2CH_2CH_2CH_3$ | cyclopropyl-$CH_2$- |
| A-567 | $CH(CH_3)CH_2CH_3$ | cyclopropyl-$CH_2$- |
| A-568 | $CH_2CH(CH_3)CH_3$ | cyclopropyl-$CH_2$- |
| A-569 | $CH(CH_2CH_3)_2$ | cyclopropyl-$CH_2$- |
| A-570 | $C(CH_3)_3$ | cyclopropyl-$CH_2$- |
| A-571 | $OCH_3$ | cyclopropyl-$CH_2$- |
| A-572 | $OCH_2CH_3$ | cyclopropyl-$CH_2$- |
| A-573 | $OCH_2CH_2CH_3$ | cyclopropyl-$CH_2$- |
| A-574 | $OCH(CH_3)_2$ | cyclopropyl-$CH_2$- |
| A-575 | $OCH_2CH_2CH_2CH_3$ | cyclopropyl-$CH_2$- |
| A-576 | $OCH(CH_3)CH_2CH_3$ | cyclopropyl-$CH_2$- |
| A-577 | $OCH_2CH(CH_3)CH_3$ | cyclopropyl-$CH_2$- |
| A-578 | $OC(CH_3)_3$ | cyclopropyl-$CH_2$- |
| A-579 | difluoromethyl | cyclopropyl-$CH_2$- |
| A-580 | trifluoromethyl | cyclopropyl-$CH_2$- |
| A-581 | 2,2-difluoroethyl | cyclopropyl-$CH_2$- |
| A-582 | 2,2,2-trifluoroethyl | cyclopropyl-$CH_2$- |
| A-583 | 2-chloro-2-fluoroethyl | cyclopropyl-$CH_2$- |
| A-584 | 2-chloro-2,2-difluoroethyl | cyclopropyl-$CH_2$- |
| A-585 | 2,2,2-trichloroethyl | cyclopropyl-$CH_2$- |
| A-586 | pentafluoroethyl | cyclopropyl-$CH_2$- |
| A-587 | 3,3,3-trifluoropropyl | cyclopropyl-$CH_2$- |
| A-588 | $CH_2CF_2CF_3$ | cyclopropyl-$CH_2$- |
| A-589 | $CF_2CF_2CF_3$ | cyclopropyl-$CH_2$- |
| A-590 | $CH(CH_3)CF_3$ | cyclopropyl-$CH_2$- |
| A-591 | $CH_2CF_2CH_3$ | cyclopropyl-$CH_2$- |
| A-592 | $CH_2C(CH_3)_2F$ | cyclopropyl-$CH_2$- |
| A-593 | $CH_2CH(CH_3)CF_3$ | cyclopropyl-$CH_2$- |

The compounds of the formula I can be prepared according to methods or in analogy to methods that are described in the prior art. The synthesis takes advantage of starting materials that are commercially available or may be prepared according to conventional procedures starting from readily available compounds. For example, compounds of the formula I wherein L is —(C=S)— can be prepared in two steps by reacting of oxadiazole amine II with compounds of type IIIa (for example acetic chloride or anhydride, LG=chlorine or acetate) in an organic solvent and in the presence of a base followed by thionylation of the obtained carboxamide with either Lawesson's reagent or diphosphorus pentasulfide, as previously described (see, for example, Journal of Organic Chemistry, 2008, 73, 9102 or European Journal of Organic Chemistry; 2015, 30, 6687).

Compounds of formula I wherein L is —S(=O)$_p$— can be prepared by reacting compounds of the formula II in the presence of a base with compounds of the formula IIIb wherein LG is preferably chlorine.

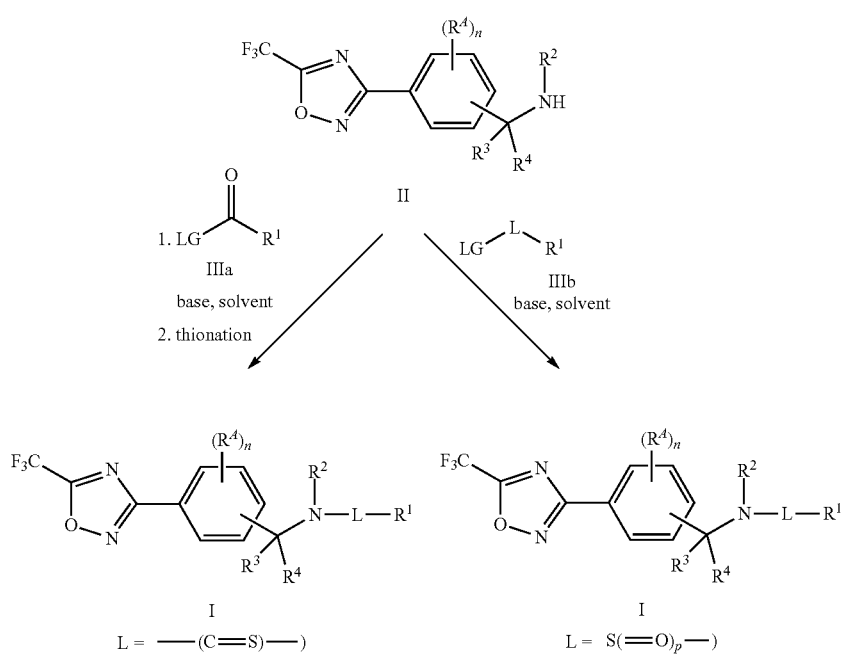

Compounds of the formula II can be prepared by reacting amidoximes of type IV with trifluoroacetic anhydride in an organic solvent, preferably an ethereal solvent at temperatures between 0° C. and 100° C., preferably at room temperature, as previously described in WO 2013/008162 or EP 276432.

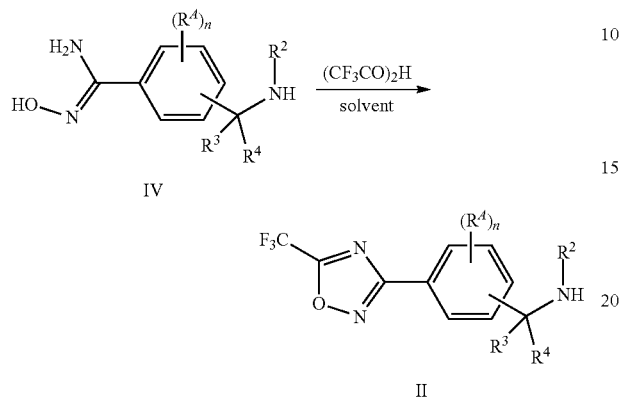

A skilled person will recognize that compounds of type IV can be accessed by treating nitriles of type V with hydroxylamine (or its hydrochloric acid salt) in an organic solvent and in the presence of a base (for precedents see for example WO 2009/074950, WO 2006/013104). Preferably ethanol and potassium carbonate. If appropriate, water may be added to enhance solubility of the reactants. The reaction is best performed at elevated temperatures, most preferably in the range between 60° C. and 80° C.

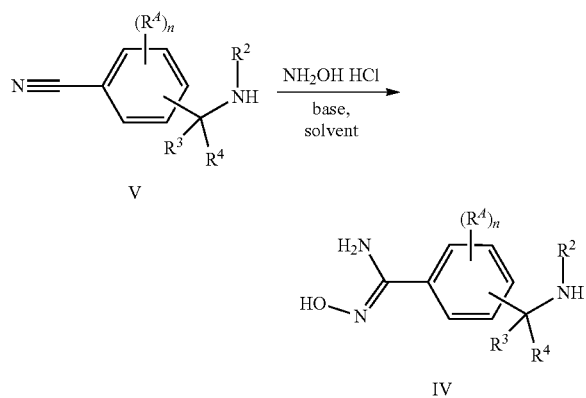

Compounds V are either commercially available or can be accessed from readily available starting materials through methods that are known to a person skilled in the art.

An alternative synthesis route to obtain compounds of formula I starts from a compound of the formula V, which is reacted with compounds IIIa or IIIb as described above. The resulting sulfonamide or carboxamide compounds VI still bears the cyano group, which is subsequently converted into the oxadiazole ring to produce compounds of the formula I via a two step cyclization reaction with hydroxylamine hydrochloride and trifluoroacetic anhydride as described above. The carboxamide may further be thionylated as described above.

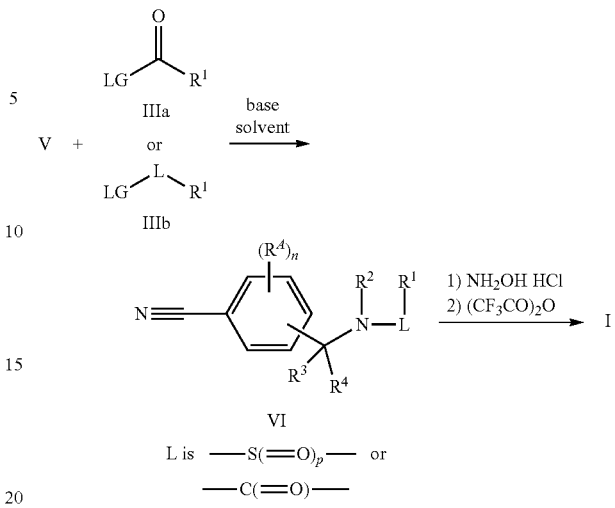

L is —S(=O)$_p$— or —C(=O)—

The compounds of the formula I or compositions comprising said compounds according to the invention and the mixtures comprising said compounds and compositions, respectively, are suitable as fungicides. They are distinguished by an outstanding effectiveness against a broad spectrum of phytopathogenic fungi, including soil-borne fungi, which derive especially from the following classes or are closely related to any of them: Ascomycota (Ascomycetes), for example, but not limited to the genus *Cochliobolus, Colletotrichum, Fusarium, Microdochium, Penicillium, Phoma, Magnaporthe, Zymoseptoria*, and *Pseudocercosporella*; Basidiomycota (Basidiomycetes), for example, but not limited to the genus *Phakospora, Puccinia, Rhizoctonia, Sphacelotheca, Tilletia, Typhula*, and *Ustilago*; Chytridiomycota (Chytridiomycetes), for example, but not limited to the genus *Chytridiales*, and *Synchytrium*; Deuteromycetes (syn. Fungi imperfecti), for example, but not limited to the genus *Ascochyta, Dlodia, Erysiphe, Fusarium, Phomopsis*, and *Pyrenophora*; Peronosporomycetes (syn. Oomycetes), for example but not limited to the genus *Peronospora, Pythium, Phytophthora*; Plasmodiophoromycetes, for example but not limited to the genus *Plasmodiophora*; Zygomycetes, for example, but not limited to the genus *Rhizopus*.

Some of the compounds of the formula I and the compositions according to the invention are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants. Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by mutagenesis or genetic engineering in order to provide a new trait to a plant or to modify an already present trait. Mutagenesis includes techniques of random mutagenesis using X-rays or mutagenic chemicals, but also techniques of targeted mutagenesis, to create mutations at a specific locus of a plant genome. Targeted mutagenesis techniques frequently use oligonucleotides or proteins like CRISPR/Cas, zinc-finger nucleases, TALENs or mega-nucleases to achieve the targeting effect. Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by mutagenesis and breeding comprise plant varieties commercially available under the name Clearfield®.

Herbicide tolerance has been created via the use of transgenes to glyphosate, glufosinate, 2,4-D, dicamba, oxynil herbicides, like bromoxynil and ioxynil, sulfonylurea herbicides, ALS inhibitors and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621, goxv247; for tolerance to glufosinate: pat and bar, for tolerance to 2,4-D: aad-1, aad-12; for tolerance to dicamba: dmo; for tolerance to oxynil herbicies: bxn; for tolerance to sulfonylurea herbicides: zm-hra, csr1-2, gm-hra, S4-HrA; for tolerance to ALS inhibitors: csr1-2; and for tolerance to HPPD inhibitors: hppdPF, W336, avhppd-03.

Transgenic corn events comprising herbicide tolerance genes include, but are not limited to, DAS40278, MON801, MON802, MON809, MON810, MON832, MON87411, MON87419, MON87427, MON88017, MON89034, NK603, GA21, MZHG0JG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes include, but are not limited to, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes include, but are not limited to, 19-51a, 31707, 42317, 81910, 281-24-236, 3006-210-23, BXN10211, BXN10215, BXN10222, BXN10224, MON1445, MON1698, MON88701, MON88913,GHB119,GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants: Transgenes which have most frequently been used are toxin genes of *Bacillus* spp. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin, such as genes coding for protease inhibitors, like CpTI and pinII, have been transferred to other plants. A further approach uses transgenes such as dvsnf7 to produce double-stranded RNA in plants.

Transgenic corn events comprising genes for insecticidal proteins or double stranded RNA include, but are not limited to, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098. Transgenic soybean events comprising genes for insecticidal proteins include, but are not limited to, MON87701, MON87751 and DAS-81419. Transgenic cotton events comprising genes for insecticidal proteins include, but are not limited to, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by using the transgene athb17, being present for example in corn event MON87403, or by using the transgene bbx32, being present for example in the soybean event MON87712.

Cultivated plants comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, such as drought, has been created by using the transgene cspB, comprised by the corn event MON87460 and by using the transgene Hahb-4, comprised by soybean event IND-ØØ41Ø-5.

Traits are frequently combined by combining genes in a transformation event or by combining different events during the breeding process resulting in a cultivated plant with stacked traits. Preferred combinations of traits are combinations of herbicide tolerance traits to different groups of herbicides, combinations of insect tolerance to different kind of insects, in particular tolerance to lepidopteran and coleopteran insects, combinations of herbicide tolerance with one or several types of insect resistance, combinations of herbicide tolerance with increased yield as well as combinations of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" (http://www.isaaa.org/gmapprovaldatabase) and the "Center for Environmental Risk Assessment (CERA)" (http://cera-gmc.org/GMCropDatabase). Further information on specific events and methods to detect them can be found for canola events MS1, MS8, RF3, GT73, MON88302, KK179 in WO01/031042, WO01/041558, WO01/041558, WO02/036831, WO11/153186, WO13/003558, for cotton events MON1445, MON15985, MON531 (MON15985), LLCotton25, MON88913, COT102, 281-24-236, 3006-210-23, COT67B, GHB614, T304-40, GHB119, MON88701, 81910 in WO02/034946, WO02/100163, WO02/100163, WO03/013224, WO04/072235, WO04/039986, WO05/103266, WO05/103266, WO06/128573, WO07/017186, WO08/122406, WO08/151780, WO12/134808, WO13/112527; for corn events GA21, MON810, DLL25, TC1507, MON863, MIR604, LY038, MON88017, 3272, 59122, NK603, MIR162, MON89034, 98140, 32138, MON87460, 5307, 4114, MON87427, DAS40278, MON87411, 33121, MON87403, MON87419 in WO98/044140, U.S. Ser. No. 02/102,582, U.S. Ser. No. 03/126,634, WO04/099447, WO04/011601, WO05/103301, WO05/061720, WO05/059103, WO06/098952, WO06/039376, US2007/292854, WO07/142840, WO07/140256, WO08/112019, WO09/103049, WO09/111263, WO10/077816, WO11/084621, WO11/062904, WO11/022469, WO13/169923, WO14/116854, WO15/053998, WO15/142571; for potato events E12, F10, J3, J55, V11, X17, Y9 in WO14/178910, WO14/178913, WO14/178941, WO14/179276, WO16/183445, WO17/062831, WO17/062825; for rice events LLRICE06, LLRICE601, LLRICE62 in WO00/026345, WO00/026356, WO00/026345; and for soybean events H7-1, MON89788, A2704-12, A5547-127, DP305423, DP356043, MON87701, MON87769, CV127, MON87705, DAS68416-4, MON87708, MON87712, SYHT0H2, DAS81419, DAS81419×DAS44406-6, MON87751 in WO04/074492, WO06/130436, WO06/108674, WO06/108675, WO08/054747, WO08/002872, WO09/064652, WO09/102873, WO10/080829, WO10/037016, WO11/066384, WO11/034704, WO12/051199, WO12/082548, WO13/016527, WO13/016516, WO14/201235.

The use of compounds I and compositions according to the invention, respectively, on cultivated plants may result in effects which are specific to a cultivated plant comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, *Mycoplasma*, viral or viroid pathogens as well as early vigour, early or delayed ripening, cold or heat tolerance as well as changed amino acid or fatty acid spectrum or content.

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchi*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasilense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuri*: Bakanae disease); *Glomerella cingulata* on vines, pome fruits and other plants and *G. gossypii* on cotton; Grain staining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici, Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni*(*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer*(black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici*(*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setosphaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

In a preferred embodiment the compounds I, their mixtures with other active compounds as defined herein and compositions thereof, respectively, are particularly suitable for controlling the following plant diseases: *Puccinia* spp. (rusts) on various plants, for example, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, and *Puccinia sorghi* (common rust) on maize, *Puccinia polysora* (southern rust) on maize; and *Phakopsoraceae* spp. on various plants, in particular *Phakopsora pachyrhizi* and *P. meibomiae* (soybean rust) on soybeans. The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "fungicidally effective amount" denotes an amount of the composition or of the compounds I, which is sufficient for controlling harmful fungi on cultivated plants or in the protection of stored products or harvest or of materials and which does not result in a substantial damage to the treated plants, the treated stored products or harvest, or to the treated materials. Such an amount can vary in a broad range and is dependent on various factors, such as the fungal species to be controlled, the treated cultivated plant, stored product, harvest or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or by Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof. Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof. Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers &

Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)

15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration Inhibitors

Inhibitors of complex III at $Q_o$ site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxy-strobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chloro-dincarb (A.1.20), famoxadone (A.1.21), fenamidone (A.1.21a), methyl-N-[2-[(1,4-dimethyl-5-phenyl-pyrazol-3-yl)oxylmethyl]phenyl]-N-methoxy-carbamate (A.1.22), metyltetrapole (A.1.25), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxymethylen)phenyl)-3-methoxy-acrylic acid methylester (A.1.38);

inhibitors of complex III at Q; site: cyazofamid (A.2.1), amisulbrom (A.2.2). [(6S,7R,8R)-8-benzyl-3-[(3-hydroxy-4-methoxy-pyridine-2-carbonyl)amino]-6-methyl-4,9-di-oxo-1,5-dioxonan-7-yl] 2-methylpropanoate (A.2.3), fenpicoxamid (A.2.4), florylpicoxamid (A.2.5);

inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), inpyrfluxam (A.3.22), pyrapropoyne (A.3.23), fluindapyr (A.3.28), methyl (E)-2-[2-[(5-cyano-2-methyl-phenoxy)methyl]phenyl]-3-methoxy-prop-2-enoate (A.3.30), isoflucypram (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethyl-indan-4-yl]pyridine-3-carboxamide (A.3.33), 2-(difluoromethyl)-N-(3-ethyl-1,1-dimethyl-indan-4-yl)pyridine-3-carboxamide (A.3.34), 2-(difluoromethyl)-N-[(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan-4-yl] pyridine-3-carboxamide (A.3.39);

other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e. g. fentin-acetate (A.4.8), fentin chloride (A.4.9) or fentin hydroxide (A.4.10); ametoctradin (A.4.11); silthiofam (A.4.12);

B) Sterol Biosynthesis Inhibitors (SBI Fungicides)

C14 demethylase inhibitors: triazoles: azaconazole (B.1.1), bitertanol (B.1.2), bromu-conazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothio-conazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 2-(2,4-difluorophenyl)-1,1-difluoro-3-(tetrazol-1-yl)-1-[5-[4-(2,2,2-trifluoroethoxy)phenyl]-2-pyridyl]propan-2-ol (B.1.31), 2-(2,4-difluorophenyl)-1,1-difluoro-3-(tetrazol-1-yl)-1-[5-[4-(trifluoromethoxy)phenyl]-2-pyridyl]propan-2-ol (B.1.32), ipfentrifluconazole (B.1.37), mefentrifluconazole (B.1.38), 2-(chloromethyl)-2-methyl-5-(p-tolylmethyl)-1-(1,2,4-triazol-1-ylmethyl) cyclopentanol (B.1.43); imidazoles: imazalil (B.1.44), pefurazoate (B.1.45), prochloraz (B.1.46), triflumizol (B.1.47); pyrimidines, pyridines, piperazines: fenarimol (B.1.49), pyrifenox (B.1.50), triforine (B.1.51), [3-(4-chloro-2-fluoro-phenyl)-5-(2,4-difluoro-phenyl) isoxazol-4-yl]-(3-pyridyl)methanol (B.1.52);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

Other Sterol biosynthesis inhibitors: chlorphenomizole (B.4.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8);

D) Inhibitors of Cell Division and Cytoskeleton tubulin inhibitors: benomyl (D.1.1), carbendazim (D.1.2), fuberidazole (D1.3), thiabendazole (D.1.4), thiophanate-methyl (D.1.5), pyridachlometyl (D.1.6), N-ethyl-2-[(3-ethynyl-8-methyl-6-quinolyl)oxy]butanamide (D.1.8), N-ethyl-2-[(3-ethynyl-8-methyl-6-quinolyl)oxy]-2-methylsulfanyl-acetamide (D.1.9), 2-[(3-ethynyl-8-methyl-6-quinolyl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl- 6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3-amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7);

E) Inhibitors of Amino Acid and Protein Synthesis methionine synthesis inhibitors: cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6);

F) Signal Transduction Inhibitors

MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acids: propamocarb (G.4.1);

inhibitors of oxysterol binding protein: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}-phenyl methanesulfonate (G.5.2), 2-{3-[2-(1-{[3,5-bis(difluoromethyl)-1H-pyrazol-1-yl]-acetyl}piperidin-4-yl) 1,3-thiazol-4-yl]-4,5-dihydro-1,2-oxazol-5-yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazo-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4-[1-[2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl]acetyl]-4-piperidyl]-N-tetralin-1-yl-pyridine-2-carboxamide (G.5.11);

H) Inhibitors with Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4-cyclopropyl-N-(2,4-dimethoxyphenyl)thiadiazole-5-carboxamide (J.1.10);

K) Unknown Mode of Action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), methasulfocarb (K.1.18), nitrapyrin (K.1.19), nitrothal-isopropyl (K.1.20), tolprocarb (K.1.21), oxin-copper (K.1.22), proquinazid (K.1.23), tebufloquin (K.1.24), tecloftalam (K.1.25), triazoxide (K.1.26), N'(4-(4-chloro-3-trifluoromethyl-phenoxy)-2,5-dimethyl-phenyl)-N-methyl-N-methyl formamidine (K.1.27), N'(4-(4-fluoro-3-trifluoromethyl-phenoxy)-2,5-dimethyl-phenyl)-N-ethyl-N-methyl formamidine (K.1.28), N'[4-[[3-[(4-chorophenyl)methyl]-1,2,4-thiadiazol-5-yl]-oxy]-2,5-dimethyl-phenyl]-N-ethyl-N-methyl-formamidine (K.1.29), N'(5-bromo-6-indan-2-yloxy-2-methyl-3-pyridyl)-N-ethyl-N-methyl-formamidine (K.1.30), N'[5-bromo-6-[1-(3,5-difluorophenyl)ethoxy]-2-methyl-3-pyridyl]-N-ethyl-N-methyl-formamidine (K.1.31), N'[5-bromo-6-(4-isopropylcyclohexoxy)-2-methyl-3-pyridyl]-N-ethyl-N-methyl-formamidine (K.1.32), N'[5-bromo-2-methyl-6-(1-phenylethoxy)-3-pyridyl]-N-ethyl-N-methyl-formamidine (K.1.33), N'(2-methyl-5-trifluoromethyl-4-(3-trimethylsilanyl-propoxy)-phenyl)-N-ethyl-N-methyl formamidine (K.1.34), N'(5-difluoromethyl-2-methyl-4-(3-trimethylsilanyl-propoxy)-phenyl)-N-ethyl-N-methyl formamidine (K.1.35), 2-(4-chlorophenyl)-N-[4-(3,4-dimethoxy-phenyl)-isoxazol-5-yl]-2-prop-2-ynyloxy-acetamide (K.1.36), 3-[5-(4-chlorophenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1-(4,6-dimethoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), ipflufenoquin (K.1.44), quinofumelin (K.1.47), 2-(6-benzyl-2-pyridyl)quinazoline (K.1.50), 2-[6-(3-fluoro-4-methoxy-phenyl)-5-methyl-2-pyridyl]quinazoline (K.1.51), dichlobentiazox (K.1.52), N'(2,5-dimethyl-4-phenoxy-phenyl)-N-ethyl-N-methyl-formamidine (K.1.53), pyrifenamine (K.1.54);

M) Growth Regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl, uniconazole;

N) Herbicides from Classes N.1 to N.15

N.1 Lipid biosynthesis inhibitors: alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-chloro-4-cyclo¬propyl-2'-fluoro[1,1'-biphenyl]-3-yl)-5-hydroxy-2,2,6,6-tetramethyl-2H-pyran-3(6H)-one (1312337-72-6); 4-(2',4'-dichloro-4-cyclopropyl[1,1'-biphenyl]-3-yl)-5-hydroxy-2, 2,6,6-tetramethyl-2H-pyran-3(6H)-one (1312337-45-3); 4-(4'-chloro-4-ethyl-2'-fluoro[1,1'-biphenyl]-3-yl)-5-hydroxy-2,2,6,6-tetramethyl-2H-pyran-3(6H)-one (1033757-93-5); 4-(2',4'-dichloro-4-ethyl[1,1'-biphenyl]-3-yl)-2,2,6,6-tetramethyl-2H-pyran-3,5(4H,6H)-dione (1312340-84-3); 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one (1312337-48-6); 5-(acetyloxy)-4-(2',4'-dichloro-4-cyclopropyl-[1,1'-biphenyl]-3-yl)-3,6-dihydro-2,2,6,6-tetramethyl-2H-pyran-3-one; 5-(acetyloxy)-4-(4'-chloro-4-ethyl-2'-fluoro[1,1'-biphenyl]-3-yl)-3,6-dihydro-2,2,6,6-tetramethyl-2H-pyran-3-one (1312340-82-1); 5-(acetyloxy)-4-(2',4'-di-chloro-4-ethyl[1,1'-biphenyl]-3-yl)-3,6-dihydro-2,2,6,6-tetramethyl-2H-pyran-3-one (1033760-55-2); 4-(4'-chloro-4-cyclopropyl-2'-fluoro[1,1'-biphenyl]-3-yl)-5,6-dihydro-2,2,6,6-tetramethl-5-oxo-2H-pyran-3-yl carbonic acid methyl ester (1312337-51-1); 4-(2',4'-dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (1312340-83-2); 4-(2',4'-di-chloro-4-ethyl,[1,1'-biphenyl]-3-yl)-5,6-dihydro-2,2,6,6-tetramethyl-5-oxo-2H-pyran-3-yl carbonic acid methyl ester (1033760-58-5); benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate, vernolate;

N.2 ALS inhibitors: amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, meta-zosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl, tritosulfuron, imazamethabenz, imazamethabenz-methyl, imazamox, imazapic, imazapyr, imazaquin, imazethapyr; cloransulam, cloransulam-methyl, diclosulam, flumetsulam, florasulam, metosulam, penoxsulam, pyrimisulfan, pyroxsulam; bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (420138-41-6), 4-[[[2-[(4,6-dimethoxy-2-pyrimidinyl)oxy]-phenyl]¬methyl]amino]-benzoic acid propyl ester (420138-40-5), N-(4-bromophenyl)-2-[(4,6-dimethoxy-2-pyrimidinyl)oxy]benzenemethanamine (420138-01-8); flucarbazone, flucarbazone-sodium, propoxycarbazone, propoxycarbazone-sodium, thiencarbazone, thiencarbazone-methyl; triafamone;

N.3 Photosynthesis inhibitors: amicarbazone; chlorotriazine; ametryn, atrazine, chloridazone, cyanazine, desmetryn, dimethametryn, hexazinone, metribuzin, prometon, prometryn, pro-pazine, simazine, simetryn, terbumeton, terbuthylazin, terbutryn, trietazin; chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, sidu-ron, tebuthiuron, thiadiazuron, desmedipham, karbutilat, phenmedipham, phenmedipham-ethyl, bromofenoxim, bromoxynil and its salts and esters, ioxynil and its salts and esters, bromacil, lenacil, terbacil, bentazon, bentazon-sodium, pyridate, pyridafol, pentanochlor, propanil; diquat, diquat-dibromide, paraquat, paraquat-dichloride, paraquat-dimetilsulfate;

N.4 protoporphyrinogen-IX oxidase inhibitors: acifluorfen, acifluorfen-sodium, azafenidin, ben-carbazone, benzfendizone, bifenox, butafenacil, carfentrazone, carfentrazone-ethyl, chlor-methoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimi-din-3-yl)phenoxy]-2-pyridyloxy]acetate (353292-31-6), N-ethyl-3-(2,6-dichloro-4-trifluoromethylphenoxy)-5-methyl-1H-pyrazole-1-carboxamide (452098-92-9), N-tetrahydrofurfuryl-3-(2,6-dichloro-4-trifluoromethylphenoxy)-5-methyl-1H-pyrazole-1-carboxamide (915396-43-9), N-ethyl-3-(2-chloro-6-fluoro-4-trifluoromethyl¬phenoxy)-5-methyl-1H-pyrazole-1-carboxamide (452099-05-7), N-tetrahydro-furfuryl-3-(2-chloro-6-fluoro-4-trifluoro-methylphenoxy)-5-methyl-1H-pyrazole-1-carboxamide (452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (1300118-96-0), 1-methyl-6-trifluoro-methyl-3-(2,2,7-tri-fluoro-3-oxo-4-prop-2-ynyl-3,4-dihydro-2H-benzo[1,4]oxazin-6-yl)-1H-pyrimidine-2,4-dione (1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (948893-00-3), 3-[7-chloro-5-fluoro-2-(trifluoromethyl)-1H-benzimidazol-4-yl]-1-methyl-6-(trifluoromethyl)-1H-pyrimidine-2,4-dione (212754-02-4);

N.5 Bleacher herbicides: beflubutamid, diflufenican, fluridone, flurochloridone, flurtamone, norflurazon, picolinafen, 4-(3-trifluoromethylphenoxy)-2-(4-trifluoromethylphenyl)pyrimidine (180608-33-7); benzobicyclon, benzofenap, bicyclopyrone, clomazone, fenquintrione, isoxaflutole, mesotrione, pyrasulfotole, pyrazolynate, pyrazoxyfen, sulcotrione, tefuryltrione, tembotrione, tolpyralate, topramezone; aclonifen, amitrole, flumeturon;

N.6 EPSP synthase inhibitors: glyphosate, glyphosate-isopropylammonium, glyposate-potassium, glyphosate-trimesium (sulfosate);

N.7 Glutamine synthase inhibitors: bilanaphos (bialaphos), bilanaphos-sodium, glufosinate, glufosinate-P, glufosinate-ammonium;

N.8 DHP synthase inhibitors: asulam;

N.9 Mitosis inhibitors: benfluralin, butralin, dinitramine, ethalfluralin, fluchloralin, oryzalin, pen-dimethalin, prodiamine, trifluralin; amiprophos, amiprophos-methyl, butamiphos; chlorthal, chlorthal-dimethyl, dithiopyr, thiazopyr, propyzamide, tebutam; carbetamide, chlorpropham, flamprop, flamprop-isopropyl, flamprop-methyl, flamprop-M-isopropyl, flamprop-M-methyl, propham;

N.10 VLCFA inhibitors: acetochlor, alachlor, butachlor, dimethachlor, dimethenamid, dimethen-amid-P, metazachlor, metolachlor, metolachlor-S, pethoxamid, pretilachlor, propachlor, prop-isochlor, thenylchlor, flufenacet, mefenacet, diphenamid, naproanilide, napropamide, napro-pamide-M, fentrazamide, anilofos, cafenstrole, fenoxasulfone, ipfencarbazone, piperophos, pyroxasulfone, isoxazoline compounds of the formulae II.1, II.2, II.3, II.4, II.5, II.6, II.7, II.8 and II.9

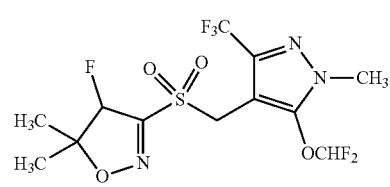

II.1

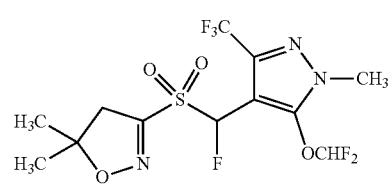

II.2

-continued

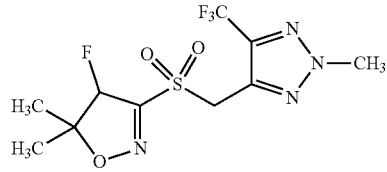

II.3

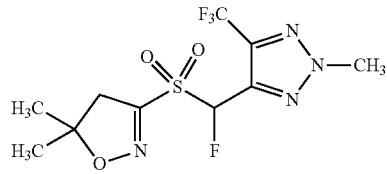

II.4

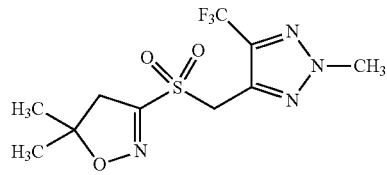

II.5

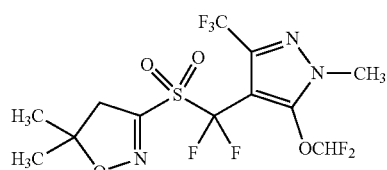

II.6

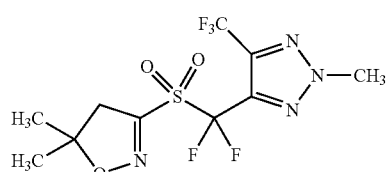

II.7

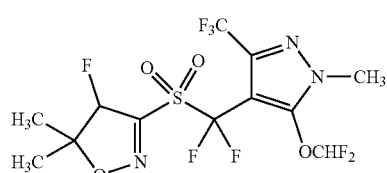

II.8

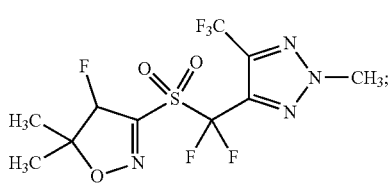

II.9

N.11 Cellulose biosynthesis inhibitors: chlorthiamid, dichlobenil, flupoxam, indaziflam, isoxaben, triaziflam, 1-cyclohexyl-5-pentafluorphenyloxy-14-[1,2,4,6]thiatriazin-3-ylamine (175899-01-1);

N.12 Decoupler herbicides: dinoseb, dinoterb, DNOC and its salts;

N.13 Auxinic herbicides: 2,4-D and its salts and esters, clacyfos, 2,4-DB and its salts and esters, aminocyclopyrachlor and its salts and esters, aminopyralid and its salts such as aminopyralid-dimethylammonium, aminopyralid(2-hydroxypropyl)ammonium and its esters, benazolin, benazolin-ethyl, chloramben and its salts and esters, clomeprop, clopy-ralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (943832-60-8); MCPA and its salts and esters, MCPA-thioethyl, MCPB and its salts and esters, mecoprop and its salts and esters, meco-prop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid, benzyl 4-amino-3-chloro-6-(4-chloro-2-fluoro-3-methoxyphenyl)-5-fluoropyridine-2-carboxylate (1390661-72-9);

N.14 Auxin transport inhibitors: diflufenzopyr, diflufenzopyr-sodium, naptalam, naptalam-sodium;

N.15 Other herbicides: bromobutide, chlorflurenol, chlorflurenol-methyl, cinmethylin, cumyluron, cyclopyrimorate (499223-49-3) and its salts and esters, dalapon, dazomet, difenzoquat, di-fenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (403640-27-7), methyl azide, methyl bromide, methyl-dymron, methyl iodide, MSMA, oleic acid, oxaziclomefone, pelargonic acid, pyributicarb, quinoclamine, tridiphane;

O) Insecticides from Classes 0.1 to 0.29

O.1 Acetylcholine esterase (AChE) inhibitors: aldicarb (O.1.1), alanycarb (O.1.2), bendiocarb (O.1.3), benfuracarb (O.1.4), butocarboxim (O.1.5), butoxycarboxim (O.1.6), carbaryl (O.1.7), carbofuran (O.1.8), carbosulfan (O.1.9), ethiofencarb (O.1.10), fenobucarb (O.1.11), formetanate (O.1.12), furathiocarb (O.1.13), isoprocarb (O.1.14), methiocarb (O.1.15), methomyl (O.1.16), metolcarb (O.1.17), oxamyl (O.1.18), pirimicarb (O.1.19), propoxur (O.1.20), thiodicarb (O.1.21), thiofanox (O.1.22), trimethacarb (O.1.23), XMC (O.1.24), xylylcarb (O.1.25), triazamate (O.1.26), acephate (O.1.27), azamethiphos (O.1.28), azinphos-ethyl (O.1.29), azinphosmethyl (O.1.30), cadusafos (O.1.31), chlorethoxyfos (O.1.32), chlorfenvinphos (O.1.33), chlormephos (O.1.34), chlorpyrifos (O.1.35), chlorpyrifos-methyl (O.1.36), coumaphos (O.1.37), cyanophos (O.1.38), demeton-S-methyl (O.1.39), diazinon (O.1.40), dichlorvos/DDVP (O.1.41), dicrotophos (O.1.42), dimethoate (O.1.43), dimethylvinphos (O.1.44), disulfoton (O.1.45), EPN (O.1.46), ethion (O.1.47), ethoprophos (O.1.48), famphur (O.1.49), fenamiphos (O.1.50), fenitrothion (O.1.51), fenthion (O.1.52), fosthiazate (O.1.53), heptenophos (O.1.54), imicyafos (O.1.55), isofenphos (O.1.56), isopropyl 0-(methoxyaminothio-phosphoryl) salicylate (O.1.57), isoxathion (O.1.58), malathion (O.1.59), mecarbam (O.1.60), methamidophos (O.1.61), methidathion (O.1.62), mevinphos (O.1.63), monocrotophos (O.1.64), naled (O.1.65), omethoate (O.1.66), oxydemeton-methyl (O.1.67), parathion (O.1.68), parathion-methyl (O.1.69), phenthoate (O.1.70), phorate (O.1.71), phosalone (O.1.72), phosmet (O.1.73), phosphamidon (O.1.74), phoxim (O.1.75), pirimiphos-methyl (O.1.76), profenofos (O.1.77), propetamphos (O.1.78), prothiofos (O.1.79), pyraclofos (O.1.80), pyridaphenthion (O.1.81), quinalphos (O.1.82), sulfotep (O.1.83), tebupirimfos (O.1.84), temephos (O.1.85), terbufos (O.1.86), tetrachlorvinphos (O.1.87), thiometon (O.1.88), triazophos (O.1.89), trichlorfon (O.1.90), vamidothion (O.1.91);

O.2 GABA-gated chloride channel antagonists: endosulfan (O.2.1), chlordane (O.2.2), ethiprole (O.2.3), fipronil (O.2.4), flufiprole (O.2.5), pyrafluprole (O.2.6), pyriprole (O.2.7);

O.3 Sodium channel modulators: acrinathrin (O.3.1), allethrin (O.3.2), d-cis-trans allethrin (O.3.3), d-trans allethrin (O.3.4), bifenthrin (O.3.5), kappa-bifenthrin (O.3.6), bioallethrin (O.3.7), bioallethrin S-cylclopentenyl (O.3.8), bioresmethrin (O.3.9), cycloprothrin (O.3.10), cyfluthrin (O.3.11), beta-cyfluthrin (O.3.12), cyhalothrin (O.3.13), lambda-cyhalothrin (O.3.14), gamma-cyhalothrin (O.3.15), cypermethrin (O.3.16), alpha-cypermethrin (O.3.17), beta-cypermethrin (O.3.18), theta-cypermethrin (O.3.19), zeta-cypermethrin (O.3.20), cyphenothrin (O.3.21), deltamethrin (O.3.22), empenthrin (O.3.23), esfenvalerate (O.3.24), etofenprox (O.3.25), fenpropathrin (O.3.26), fenvalerate (O.3.27), flucythrinate (O.3.28), flumethrin (O.3.29), tau-fluvalinate (O.3.30), halfenprox (O.3.31), heptafluthrin (O.3.32), imiprothrin (O.3.33), meperfluthrin (O.3.34), metofluthrin (O.3.35), momfluorothrin (O.3.36), epsilon-momfluorothrin (O.3.37), permethrin (O.3.38), phenothrin (O.3.39), prallethrin (O.3.40), profluthrin (O.3.41), pyrethrin (pyrethrum) (O.3.42), resmethrin (O.3.43), silafluofen (O.3.44), tefluthrin (O.3.45), kappa-tefluthrin (O.3.46), tetramethylfluthrin (O.3.47), tetramethrin (O.3.48), tralomethrin (O.3.49), transfluthrin (O.3.50), DDT (O.3.51), methoxychlor (O.3.52);

O.4 Nicotinic acetylcholine receptor agonists (nAChR): acetamiprid (O.4.1), clothianidin (O.4.2), cycloxaprid (O.4.3), dinotefuran (O.4.4), imidacloprid (O.4.5), nitenpyram (O.4.6), thiacloprid (O.4.7), thiamethoxam (O.4.8), 4,5-dihydro-N-nitro-1-(2-oxiranylmethyl)-1H-imidazol-2-amine (O.4.9), (2E)-1-[(6-chloropyridin-3-yl)methyl]-N'-nitro-2-pentylidene-hydrazinecarboximid-amide (O.4.10), 1-[(6-chloropyridin-3-yl)methyl]-7-methyl-8-nitro-5-propoxy-1,2,3,5,6,7-hexahydroimidazo[1,2-a]pyridine (O.4.11), nicotine (O.4.12), sulfoxaflor (O.4.13), flupyradifurone (O.4.14), triflumezopyrim (O.4.15);

O.5 Nicotinic acetylcholine receptor allosteric activators: spinosad (O.5.1), spinetoram (O.5.2);

O.6 Chloride channel activators: abamectin (O.6.1), emamectin benzoate (O.6.2), ivermectin (O.6.3), lepimectin (O.6.4), milbemectin (O.6.5);

O.7 Juvenile hormone mimics: hydroprene (O.7.1), kinoprene (O.7.2), methoprene (O.7.3), fenoxycarb (O.7.4), pyriproxyfen (O.7.5);

O.8 miscellaneous non-specific (multi-site) inhibitors: methyl bromide (O.8.1) and other alkyl halides, chloropicrin (O.8.2), sulfuryl fluoride (O.8.3), borax (O.8.4), tartar emetic (O.8.5);

O.9 Chordotonal organ TRPV channel modulators: pymetrozine (O.9.1), pyrifluquinazon (O.9.2), flonicamid (O.9.3);

O.10 Mite growth inhibitors: clofentezine (O.10.1), hexythiazox (O.10.2), diflovidazin (O.10.3), etoxazole (O.10.4);

O.11 Microbial disruptors of insect midgut membranes: *Bacillus thuringiensis, Bacillus sphaericus* and the insecticidal proteins they produce: *Bacillus thuringiensis* subsp. *lsraelensis* (O.11.1), *Bacillus sphaericus* (O.11.2), *Bacillus thuringiensis* subsp. *aizawai* (O.11.3), *Bacillus thuringiensis* subsp. *kurstaki* (O.11.4), *Bacillus thuringiensis* subsp. *tenebrionis* (O.11.5), the Bt crop proteins: Cry1Ab (O.11.6), Cry1Ac (O.11.7), Cry1Fa (O.11.8), Cry2Ab (O.11.9), mCry3A (O.11.10), Cry3Ab (O.11.11), Cry3Bb (O.11.12), Cry34/35Ab1 (O.11.13);

O.12 Inhibitors of mitochondrial ATP synthase: diafenthiuron (O.12.1), azocyclotin (O.12.2), cyhexatin (O.12.3), fenbutatin oxide (O.12.4), propargite (O.12.5), tetradifon (O.12.6);

O.13 Uncouplers of oxidative phosphorylation via disruption of the proton gradient: chlorfenapyr (O.13.1), DNOC (O.13.2), sulfluramid (O.13.3);

O.14 Nicotinic acetylcholine receptor (nAChR) channel blockers: bensultap (O.14.1), cartap hydrochloride (O.14.2), thiocyclam (O.14.3), thiosultap sodium (O.14.4);

O.15 Inhibitors of the chitin biosynthesis type 0: bistrifluron (O.15.1), chlorfluazuron (O.15.2), diflubenzuron (O.15.3), flucycloxuron (O.15.4), flufenoxuron (O.15.5), hexaflumuron (O.15.6), lufenuron (O.15.7), novaluron (O.15.8), noviflumuron (O.15.9), teflubenzuron (O.15.10), triflumuron (O.15.11);

O.16 Inhibitors of the chitin biosynthesis type 1: buprofezin (O.16.1);

O.17 Moulting disruptors: cyromazine (O.17.1);

O.18 Ecdyson receptor agonists: methoxyfenozide (O.18.1), tebufenozide (O.18.2), halofenozide (O.18.3), fufenozide (O.18.4), chromafenozide (O.18.5);

O.19 Octopamin receptor agonists: amitraz (O.19.1);

O.20 Mitochondrial complex III electron transport inhibitors: hydramethylnon (O.20.1), acequinocyl (O.20.2), fluacrypyrim (O.20.3), bifenazate (O.20.4);

O.21 Mitochondrial complex I electron transport inhibitors: fenazaquin (O.21.1), fenpyroximate (O.21.2), pyrimidifen (O.21.3), pyridaben (O.21.4), tebufenpyrad (O.21.5), tolfenpyrad (O.21.6), rotenone (O.21.7);

O.22 Voltage-dependent sodium channel blockers: indoxacarb (O.22.1), metaflumizonev (O.22.2), 2-[2-(4-cyanophenyl)-1-[3-(trifluoromethyl)phenyl]ethylidene]-N-[4-(difluoromethoxy)phenyl]-hydrazinecarboxamide (O.22.3), N-(3-chloro-2-methylphenyl)-2-[(4-chlorophenyl)-[4-[methyl(methylsulfonyl)amino]phenyl]methylene]-hydrazinecarboxamide (O.22.4);

O.23 Inhibitors of the of acetyl CoA carboxylase: spirodiclofen (O.23.1), spiromesifen (O.23.2), spirotetramat (O.23.3), spiropidion (O.23.4);

O.24 Mitochondrial complex IV electron transport inhibitors: aluminium phosphide (O.24.1), calcium phosphide (O.24.2), phosphine (O.24.3), zinc phosphide (O.24.4), cyanide (O.24.5);

O.25 Mitochondrial complex II electron transport inhibitors: cyenopyrafen (O.25.1), cyflumetofen (O.25.2);

O.26 Ryanodine receptor-modulators: flubendiamide (O.26.1), chlorantraniliprole (O.26.2), cyantraniliprole (O.26.3), cyclaniliprole (O.26.4), tetraniliprole (O.26.5), (R)-3-chloro-N$^1$-{2-methyl-4-[1,2,2,2-tetrafluoro-1-(trifluoromethyl)ethyl]phenyl}-N$^2$-(1-methyl-2-methylsulfonylethyl)phthalamide (O.26.6), (S)-3-chloro-N$^1$-{2-methyl-4-[1,2,2,2-tetrafluoro-1-(trifluoromethyl)ethyl]phenyl}-N$^2$-(1-methyl-2-methylsulfonylethyl) phthalamide (O.26.7), methyl-2-[3,5-dibromo-2-({[3-bromo-1-(3-chloropyridin-2-yl)-1H-pyrazol-5-yl]carbonyl}-amino)benzoyl]-1,2-dimethylhydrazinecarboxylate (O.26.8), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.26.9), N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide (O.26.10), N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide (O.26.11), N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.26.12), N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide (O.26.13), N-[2-(5-amino-1,3,4-thiadiazol-2-yl)-4-chloro-6-methylphenyl]-3-bromo-1-(3-chloro-2-pyridinyl)-1H-pyrazole-5-carboxamide (O.26.14), 3-chloro-1-(3-chloro-2-pyridinyl)-N-[2,4-dichloro-6-[[(1-cyano-1-methylethyl)amino]carbonyl]phenyl]-1H-pyrazole-5-carboxamide (O.26.15), 3-bromo-N-[2,4-dichloro-6-(methylcarbamoyl)phenyl]-1-(3,5-dichloro-2-pyridyl)-1H-pyrazole-5-carboxamide (O.26.16), N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (O.26.17), cyhalodiamide (O.26.18);

O.27: Chordotonal organ Modulators—undefined target site: flonicamid (O.27.1);

O.28. insecticidal active compounds of unknown or uncertain mode of action: afidopyropen (O.28.1), afoxolaner (O.28.2), azadirachtin (O.28.3), amidoflumet (O.28.4), benzoximate (O.28.5), broflanilide (O.28.6), bromopropylate (O.28.7), chinomethionat (O.28.8), cryolite (O.28.9), dicloromezotiaz (O.28.10), dicofol (O.28.11), flufenerim (O.28.12), flometoquin (O.28.13), fluensulfone (O.28.14), fluhexafon (O.28.15), fluopyram (O.28.16), fluralaner (O.28.17), metoxadiazone (O.28.18), piperonyl butoxide (O.28.19), pyflubumide (O.28.20), pyridalyl (O.28.21), tioxazafen (O.28.22), 11-(4-chloro-2,6-dimethylphenyl)-12-hydroxy-1,4-dioxa-9-azadispiro[4.2.4.2]-tetradec-11-en-10-one, 3-(4'-fluoro-2,4-dimethylbiphenyl-3-yl)-4-hydroxy-8-oxa-1-azaspiro[4.5]dec-3-en-2-one, 1-[2-fluoro-4-methyl-5-[(2,2,2-trifluoroethyl)sulfinyl]phenyl]-3-(trifluoromethyl)-1H-1,2,4-triazole-5-amine (O.28.23), *Bacillus firmus* 1-1582 (O.28.24), flupyrimin (O.28.25), fluazaindolizine (O.28.26), 4-[5-(3,5-di-chlorophenyl)-5-(trifluoromethyl)-4H-isoxazol-3-yl]-2-methyl-N-(1-oxothietan-3-yl) benzamide (O.28.27), fluxametamide (O.28.28), 5-[3-[2,6-dichloro-4-(3,3-dichloroallyloxy)phenoxy]propoxy]-1H-pyrazole (O.28.1), 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide (O.28.29), 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide (O.28.30), N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide (O.28.31), N-[5-[[2-bromo-6-chloro-4-[2,2,2-tri-fluoro-1-hydroxy-1-(trifluoromethyl)ethyl]phenyl]carbamoyl]-2-cyano-phenyl]-4-cyano-2-methyl-benzamide (O.28.32), N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide (O.28.33), 4-cyano-N-[2-cyano-5-[[2,6-dichloro-4-[1,2,2,3,3,3-hexafluoro-1-(trifluoromethyl)propyl]phenyl]-carbamoyl]phenyl]-2-methyl-benzamide (O.28.34), 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide (O.28.35), N-[5-[[2-bromo-6-chloro-4-[1,2,2,2-tetrafluoro-1-(trifluoromethyl)ethyl]phenyl]-carbamoyl]-2-cyano-phenyl]-4-cyano-2-methyl-benzamide (O.28.36); 2-(1,3-dioxan-2-yl)-6-[2-(3-pyridinyl)-5-thiazolyl]-pyridine (O.28.37), 2-[6-[2-(5-fluoro-3-pyridinyl)-5-thiazolyl]-2-pyridinyl]-pyrimidine (O.28.38), 2-[6-[2-(3-pyridinyl)-5-thiazolyl]-2-pyridinyl]-pyrimidine (O.28.39), N-methylsulfonyl-6-[2-(3-pyridyl)thiazol-5-yl]pyridine-2-carboxamide (O.28.40), N-methylsulfonyl-6-[2-(3-pyridyl)thiazol-5-yl]pyridine-2-carboxamide (O.28.41), 1-[(6-chloro-3-pyridinyl) methyl]-1,2,3,5,6,7-hexahydro-5-methoxy-7-methyl-8-nitro-imidazo[1,2-a]pyridine (O.28.42), 1-[(6-chloropyridin-3-yl)methyl]-7-methyl-8-nitro-1,2,3,5,6,7-hexahydroimidazo[1,2-a]pyridin-5-ol (O.28.43), 1-isopropyl-N,5-dimethyl-N-pyridazin-4-yl-pyrazole-4-carboxamide (O.28.44), 1-(1,2-dimethylpropyl)-N-ethyl-5-methyl-N-pyridazin-4-yl-pyrazole-4-carboxamide (O.28.45), N,5-dimethyl-N-pyridazin-4-yl-1-(2,2,2-trifluoro-1-methyl-ethyl)pyrazole-4-carboxamide (O.28.46), 1-[1-(1-cyanocyclopropyl)ethyl]-N-ethyl-5-methyl-N-pyridazin-4-yl-pyrazole-4-carboxamide (O.28.47), N-ethyl-1-(2-fluoro-1-methyl-propyl)-5-methyl-N-pyridazin-4-yl-pyrazole-4-carboxamide (O.28.48), 1-(1,2-dimethylpropyl)-N,5-dimethyl-N-pyridazin-4-yl-pyrazole-4-carboxamide (O.28.49), 1-[1-(1-cyanocyclopropyl)ethyl]-N,5-di-methyl-N-pyridazin-4-yl-pyrazole-4-carboxamide (O.28.50), N-methyl-1-(2-fluoro-1-methyl-propyl]-5-methyl-N-pyridazin-4-yl-pyrazole-4-carboxamide (O.28.51), 1-(4,4-difluorocyclohexyl)-N-ethyl-5-methyl-N-pyridazin-4-yl-pyrazole-4-carboxamide (O.28.52), 1-(4,4-difluorocyclohexyl)-N,5-dimethyl-N-pyridazin-4-yl-pyrazole-4-carboxamide (O.28.53), N-(1-methylethyl)-2-(3-pyridinyl)-2H-indazole-4-carboxamide (O.28.54), N-cyclopropyl-2-(3-pyridinyl)-2H-indazole-4-carboxamide (O.28.55), N-cyclohexyl-2-(3-pyridinyl)-2H-indazole-4-carboxamide (O.28.56), 2-(3-pyridinyl)-N-(2,2,2-trifluoroethyl)-2H-indazole-4-carboxamide (O.28.57), 2-(3-pyridinyl)-N-[(tetrahydro-2-furanyl)methyl]-2H-indazole-5-carboxamide (O.28.58), methyl 2-[[2-(3-pyridinyl)-2H-indazol-5-yl]carbonyl]hydrazinecarboxylate (O.28.59), N-[(2,2-difluorocyclopropyl)methyl]-2-(3-pyridinyl)-2H-indazole-5-carboxamide (O.28.60), N-(2,2-difluoropropyl)-2-(3-pyridinyl)-2H-indazole-5-carboxamide (O.28.61), 2-(3-pyridinyl)-N-(2-pyrimidinylmethyl)-2H-indazole-5-carboxamide (O.28.62), N-[(5-methyl-2-pyrazinyl)methyl]-2-(3-pyridinyl)-2H-indazole-5-carboxamide (O.28.63), tyclopyrazoflor (O.28.64), sarolaner (O.28.65), lotilaner (O.28.66), N-[4-chloro-3-[[(phenylmethyl)amino]carbonyl]phenyl]-1-methyl-3-(1,1,2,2,2-penta-fluoroethyl)-4-(trifluoromethyl)-1H-pyrazole-5-carboxamide (O.28.67), M.UN.22a 2-(3-ethylsulfonyl-2-pyridyl)-3-methyl-6-(trifluoromethyl)imidazo[4,5-b]pyridine (O.28.68), 2-[3-ethylsulfonyl-5-(trifluoromethyl)-2-pyridyl]-3-methyl-6-(trifluoromethyl)imidazo[4,5-b]pyridine (O.28.69), 4-[5-(3,5-dichlorophenyl)-5-(trifluoromethyl)-4H-isoxazol-3-yl]-N-[(4R)-2-ethyl-3-oxo-isoxazolidin-4-yl]-2-methyl-benzamide (O.28.70), 4-[5-(3,5-dichloro-4-fluorophenyl)-5-(trifluoromethyl)-4H-isoxazol-3-yl]-N-[(4R)-2-ethyl-3-oxo-isoxazolidin-4-yl]-2-methyl-benzamide (O.28.71), N-[4-chloro-3-(cyclopropylcarbamoyl)phenyl]-2-methyl-5-(1,1,2,2,2-pentafluoroethyl)-4-(trifluoromethyl)pyrazole-3-carboxamide (O.28.72), N-[4-chloro-3-[(1-cy-anocyclopropyl)carbamoyl]phenyl]-2-methyl-5-(1,1,2,2,2-pentafluoroethyl)-4-(trifluoromethyl)-pyrazole-3-carboxamide (O.28.73), acynonapyr (O.28.74), benzpyrimoxan (O.28.75), chloro-N-(1-cyanocyclopropyl)-5-[1-[2-methyl-5-(1,1,2,2,2-pentafluoroethyl)-4-(trifluoromethyl)pyrazol-3-yl]pyrazol-4-yl]benzamide (O.28.76), oxazosulfyl (O.28.77), [(2S,3R,4R,5S,6S)-3,5-dimethoxy-6-methyl-4-propoxy-tetrahydropyran-2-yl]-N-[4-[1-[4-(tri-fluoromethoxy)phenyl]-1,2,4-triazol-3-yl]phenyl]carbamate (O.28.78), [(2S,3R,4R,5S,6S)-3,4,5-trimethoxy-6-methyl-tetrahydropyran-2-yl] N-[4-[1-[4-(trifluoro-methoxy)phenyl]-1,2,4-triazol-3-yl]phenyl]carbamate (O.28.79), [(2S,3R,4R,5S,6S)-3,5-dimethoxy-6-methyl-4-propoxy-tetrahydropyran-2-yl]-N-[4-[1-[4-(1,1,2,2,2-pentafluoroethoxy)phenyl]-1,2,4-triazol-3-yl]phenyl] carbamate (O.28.80), [(2S,3R,4R,5S,6S)-3,4,5-trimethoxy-6-methyl-tetrahydropyran-2-yl]-N-[4-[1-[4-(1,1,2,2,2-penta-fluoroethoxy)phenyl]-1,2,4-triazol-3-yl]phenyl]carbamate (O.28.81), (2Z)-3-(2-isopropylphenyl)-2-[(E)-[4-[1-[4-(1,1,2,2,2-pentafluoroethoxy)phenyl]-1,2,4-triazol-3-yl]phenyl]methylenehydrazono]thiazolidin-4-one (O.28.82).

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441). Some compounds are identified by their CAS Registry Number which is separated by hyphens into three parts, the first consisting from two up to seven digits, the second consisting of two digits, and the third consisting of a single digit The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day.

In the binary mixtures and compositions according to the invention the weight ratio of the component 1) and the component 2) generally depends from the properties of the active components used, usually it is in the range of from 1:10,000 to 10,000:1, often it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Accordingly, the present invention furthermore relates to mixtures comprising one compound of the formula I (component 1, a group represented by the expression "(1)") and one pesticide II (component 2), wherein pesticide II is an active ingredients selected from the groups A) to O) defined above.

Further embodiments B-1 to B-683 listed in Table B below relate to mixtures comprising as active components one of the in the present specification individualized compounds of the formula I, which is selected from the group of compounds I.A.A-1 to I.A.A-593, I.B.A-1 to I.B.A-593, I.C.A-1 to I.C.A-593, I.D.A-1 to I.D.A-593, I.E.A-1 to I.E.A-593, I.F.A-1 to I.F.A-593, I.G.A-1 to I.G.A-593, I.H.A-1 to I.H.A-593, I.J.A-1 to I.J.A-593 and I.K.A-1 to I.K.A-593 defined in tables 1 to 10 (component 1, a group represented by the expression "(1)") and one pesticide II selected from the groups A) to O) as defined herein (component 2, for example, (A.1.1) or azoxystrobin, in embodiment B-1).

Further embodiments B-1 to B-683 listed in Table B below relate to the mixtures comprising as active components one of the in the present specification individualized compounds of the formula I, which is selected from the group of compounds Ex-1 to Ex-47 of formula I as defined in Table I below (component 1, a group represented by the expression "(1)") and one pesticide II selected from the groups A) to O) as defined herein (component 2, for example, (A.1.1) or azoxystrobin, in embodiment B-1).

Preferably, the compositions described in Table B comprise the active components in synergistically effective amounts.

Table B:

B-1: (I)+(A.1.1), B-2: (I)+(A.1.2), B-3: (I)+(A.1.3), B-4: (I)+(A.1.4), B-5: (I)+(A.1.5), B-6: (I)+(A.1.6), B-7: (I)+(A.1.7), B-8: (I)+(A.1.8), B-9: (I)+(A.1.9), B-10: (I)+(A.1.10), B-11: (I)+(A.1.11), B-12: (I)+(A.1.12), B-13: (I)+(A.1.13), B-14: (I)+(A.1.14), B-15: (I)+(A.1.15), B-16: (I)+(A.1.16), B-17: (I)+(A.1.17), B-18: (I)+(A.1.18), B-19: (I)+(A.1.19), B-20: (I)+(A.1.20), B-21: (I)+(A.1.21), B-22: (I)+(A.1.21a), B-23: (I)+(A.1.22), B-24: (I)+(A.1.25), B-25: (I)+(A.1.34), B-26: (I)+(A.1.35), B-27: (I)+(A.1.36), B-28: (I)+(A.1.37), B-29: (I)+(A.1.38), B-30: (I)+(A.2.1), B-31: (I)+(A.2.2), B-32: (I)+(A.2.3), B-33: (I)+(A.2.4), B-34: (I)+(A.2.5), B-35: (I)+(A.3.1), B-36: (I)+(A.3.2), B-37: (I)+(A.3.3), B-38: (I)+(A.3.4), B-39: (I)+(A.3.5), B-40: (I)+(A.3.6), B-41: (I)+(A.3.7), B-42: (I)+(A.3.8), B-43: (I)+(A.3.9), B-44: (I)+(A.3.10), B-45: (I)+(A.3.11), B-46: (I)+(A.3.12), B-47: (I)+(A.3.13), B-48: (I)+(A.3.14), B-49: (I)+(A.3.15), B-50: (I)+(A.3.16), B-51: (I)+(A.3.17), B-52: (I)+(A.3.18), B-53: (I)+(A.3.19), B-54: (I)+(A.3.20), B-55: (I)+(A.3.21), B-56: (I)+(A.3.22), B-57: (I)+(A.3.23), B-58: (I)+(A.3.24), B-59: (I)+(A.3.25), B-60: (I)+(A.3.26), B-61: (I)+(A.3.27), B-62: (I)+(A.3.28), B-63: (I)+(A.3.30), B-64: (I)+(A.3.31), B-65: (I)+(A.3.32), B-66: (I)+(A.3.33), B-67: (I)+(A.3.34), B-68: (I)+(A.3.35), B-69: (I)+(A.3.36), B-70: (I)+(A.3.37), B-71: (I)+(A.3.38), B-72: (I)+(A.3.39), B-73: (I)+(A.4.1), B-74: (I)+(A.4.2), B-75: (I)+(A.4.3), B-76: (I)+(A.4.4), B-77: (I)+(A.4.5), B-78: (I)+(A.4.6), B-79: (I)+(A.4.7), B-80: (I)+(A.4.8), B-81: (I)+(A.4.9), B-82: (I)+(A.4.10), B-83: (I)+(A.4.11), B-84: (I)+(A.4.12), B-85: (B.1.1), B-86: (I)+(B.1.2), B-87: (I)+(B.1.3), B-88: (I)+(B.1.4), B-89: (I)+(B.1.5), B-90: (I)+(B.1.6), B-91: (I)+(B.1.7), B-92: (I)+(B.1.8), B-93: (I)+(B.1.9), B-94: (I)+(B.1.10), B-95: (I)+(B.1.11), B-96: (I)+(B.1.12), B-97: (I)+(B.1.13), B-98: (I)+(B.1.14), B-99: (I)+(B.1.15), B-100: (I)+(B.1.16), B-101: (I)+(B.1.17), B-102: (I)+(B.1.18), B-103: (I)+(B.1.19), B-104: (I)+(B.1.20), B-105: (I)+(B.1.21), B-106: (I)+(B.1.22), B-107: (I)+(B.1.23), B-108: (I)+(B.1.24), B-109: (I)+(B.1.25), B-110: (I)+(B.1.26), B-111: (I)+(B.1.27), B-112: (I)+(B.1.28), B-113: (I)+(B.1.29), B-114: (I)+(B.1.30), B-115: (I)+(B.1.31), B-116: (I)+(B.1.32), B-117: (I)+(B.1.37), B-118: (I)+(B.1.38), B-119: (I)+(B.1.39), B-120: (I)+(B.1.40), B-121: (I)+

(B.1.41), B-122: (I)+(B.1.42), B-123: (I)+(B.1.43), B-124: (I)+(B.1.44), B-125: (I)+(B.1.45), B-126: (I)+(B.1.46), B-127: (I)+(B.1.47), B-128: (I)+(B.1.48), B-129: (I)+(B.1.49), B-130: (I)+(B.1.50), B-131: (I)+(B.1.51), B-132: (I)+(B.1.52), B-133: (I)+(B.2.1), B-134: (I)+(B.2.2), B-135: (I)+(B.2.3), B-136: (I)+(B.2.4), B-137: (I)+(B.2.5), B-138: (I)+(B.2.6), B-139: (I)+(B.2.7), B-140: (I)+(B.2.8), B-141: (I)+(B.3.1), B-142: (I)+(B.4.1), B-143: (I)+(C.1.1), B-144: (I)+(C.1.2), B-145: (I)+(C.1.3), B-146: (I)+(C.1.4), B-147: (I)+(C.1.5), B-148: (I)+(C.1.6), B-149: (I)+(C.1.7), B-150: (I)+(C.2.1), B-151: (I)+(C.2.2), B-152: (I)+(C.2.3), B-153: (I)+(C.2.4), B-154: (I)+(C.2.5), B-155: (I)+(C.2.6), B-156: (I)+(C.2.7), B-157: (I)+(C.2.8), B-158: (I)+(D.1.1), B-159: (I)+(D.1.2), B-160: (I)+(D.1.3), B-161: (I)+(D.1.4), B-162: (I)+(D.1.5), B-163: (I)+(D.1.6), B-164: (I)+(D.1.7), B-165: (I)+(D.1.8), B-166: (I)+(D.1.9), B-167: (I)+(D.1.10), B-168: (I)+(D.1.11), B-169: (I)+(D.1.12), B-170: (I)+(D.1.13), B-171: (I)+(D.1.14), B-172: (I)+(D.1.15), B-173: (I)+(D.1.16), B-174: (I)+(D.2.1), B-175: (I)+(D.2.2), B-176: (I)+(D.2.3), B-177: (I)+(D.2.4), B-178: (I)+(D.2.5), B-179: (I)+(D.2.6), B-180: (I)+(D.2.7), B-181: (I)+(E.1.1), B-182: (I)+(E.1.2), B-183: (I)+(E.1.3), B-184: (I)+(E.2.1), B-185: (I)+(E.2.2), B-186: (I)+(E.2.3), B-187: (I)+(E.2.4), B-188: (I)+(E.2.5), B-189: (I)+(E.2.6), B-190: (I)+(F.1.1), B-191: (I)+(F.1.2), B-192: (I)+(F.1.3), B-193: (I)+(F.1.4), B-194: (I)+(F.1.5), B-195: (I)+(F.2.1), B-196: (I)+(G.1.1), B-197: (I)+(G.1.2), B-198: (I)+(G.1.3), B-199: (I)+(G.1.4), B-200: (I)+(G.2.1), B-201: (I)+(G.2.2), B-202: (I)+(G.2.3), B-203: (I)+(G.2.4), B-204: (I)+(G.2.5), B-205: (I)+(G.2.6), B-206: (I)+(G.2.7), B-207: (I)+(G.3.1), B-208: (I)+(G.3.2), B-209: (I)+(G.3.3), B-210: (I)+(G.3.4), B-211: (I)+(G.3.5), B-212: (I)+(G.3.6), B-213: (I)+(G.3.7), B-214: (I)+(G.4.1), B-215: (I)+(G.5.1), B-216: (I)+(G.5.2), B-217: (I)+(G.5.3), B-218: (I)+(G.5.4), B-219: (I)+(G.5.5), B-220: (I)+(G.5.6), B-221: (I)+(G.5.7), B-222: (I)+(G.5.8), B-223: (I)+(G.5.9), B-224: (I)+(G.5.10), B-225: (I)+(G.5.11), B-226: (I)+(H.1.1), B-227: (I)+(H.1.2), B-228: (I)+(H.1.3), B-229: (I)+(H.1.4), B-230: (I)+(H.1.5), B-231: (I)+(H.1.6), B-232: (I)+(H.1.7), B-233: (I)+(H.2.1), B-234: (I)+(H.2.2), B-235: (I)+(H.2.3), B-236: (I)+(H.2.4), B-237: (I)+(H.2.5), B-238: (I)+(H.2.6), B-239: (I)+(H.2.7), B-240: (I)+(H.2.8), B-241: (I)+(H.2.9), B-242: (I)+(H.3.1), B-243: (I)+(H.3.2), B-244: (I)+(H.3.3), B-245: (I)+(H.3.4), B-246: (I)+(H.3.5), B-247: (I)+(H.3.6), B-248: (I)+(H.3.7), B-249: (I)+(H.3.8), B-250: (I)+(H.3.9), B-251: (I)+(H.3.10), B-252: (I)+(H.3.11), B-253: (I)+(H.4.1), B-254: (I)+(H.4.2), B-255: (I)+(H.4.3), B-256: (I)+(H.4.4), B-257: (I)+(H.4.5), B-258: (I)+(H.4.6), B-259: (I)+(H.4.7), B-260: (I)+(H.4.8), B-261: (I)+(H.4.9), B-262: (I)+(H.4.10), B-263: (I)+(I.1.1), B-264: (I)+(I.1.2), B-265: (I)+(I.2.1), B-266: (I)+(I.2.2), B-267: (I)+(I.2.3), B-268: (I)+(I.2.4), B-269: (I)+(I.2.5), B-270: (I)+(J.1.1), B-271: (I)+(J.1.2), B-272: (I)+(J.1.3), B-273: (I)+(J.1.4), B-274: (I)+(J.1.5), B-275: (I)+(J.1.6), B-276: (I)+(J.1.7), B-277: (I)+(J.1.8), B-278: (I)+(J.1.9), B-279: (I)+(J.1.10), B-280: (I)+(K.1.1), B-281: (I)+(K.1.2), B-282: (I)+(K.1.3), B-283: (I)+(K.1.4), B-284: (I)+(K.1.5), B-285: (I)+(K.1.6), B-286: (I)+(K.1.7), B-287: (I)+(K.1.8), B-288: (I)+(K.1.9), B-289: (I)+(K.1.10), B-290: (I)+(K.1.11), B-291: (I)+(K.1.12), B-292: (I)+(K.1.13), B-293: (I)+(K.1.14), B-294: (I)+(K.1.15), B-295: (I)+(K.1.16), B-296: (I)+(K.1.17), B-297: (I)+(K.1.18), B-298: (I)+(K.1.19), B-299: (I)+(K.1.20), B-300: (I)+(K.1.21), B-301: (I)+(K.1.22), B-302: (I)+(K.1.23), B-303: (I)+(K.1.24), B-304: (I)+(K.1.25), B-305: (I)+(K.1.26), B-306: (I)+(K.1.27), B-307: (I)+(K.1.28), B-308: (I)+(K.1.29), B-309: (I)+(K.1.30), B-310: (I)+(K.1.31), B-311: (I)+(K.1.32), B-312: (I)+(K.1.33), B-313: (I)+(K.1.34), B-314: (I)+(K.1.35), B-315: (I)+(K.1.36), B-316: (I)+(K.1.37), B-317: (I)+(K.1.38), B-318: (I)+(K.1.39), B-319: (I)+(K.1.40), B-320: (I)+(K.1.41), B-321: (I)+(K.1.42), B-322: (I)+(K.1.43), B-323: (I)+(K.1.44), B-324: (I)+(K.1.45), B-325: (I)+(K.1.46), B-326: (I)+(K.1.47), B-327: (I)+(K.1.48), B-328: (I)+(K.1.49), B-329: (I)+(K.1.50), B-330: (I)+(K.1.51), B-331: (I)+(K.1.52), B-332: (I)+(K.1.53), B-333: (I)+(K.1.54), B-334: (I)+(O.1.1), B-335: (I)+(O.1.2), B-336: (I)+(O.1.3), B-337: (I)+(O.1.4), B-338: (I)+(O.1.5), B-339: (I)+(O.1.6), B-340: (I)+(O.1.7), B-341: (I)+(O.1.8), B-342: (I)+(O.1.9), B-343: (I)+(O.1.10), B-344: (I)+(O.1.11), B-345: (I)+(O.1.12), B-346: (I)+(O.1.13), B-347: (I)+(O.1.14), B-348: (I)+(O.1.15), B-349: (I)+(O.1.16), B-350: (I)+(O.1.17), B-351: (I)+(O.1.18), B-352: (I)+(O.1.19), B-353: (I)+(O.1.20), B-354: (I)+(O.1.21), B-355: (I)+(O.1.22), B-356: (I)+(O.1.23), B-357: (I)+(O.1.24), B-358: (I)+(O.1.25), B-359: (I)+(O.1.26), B-360: (I)+(O.1.27), B-361: (I)+(O.1.28), B-362: (I)+(O.1.29), B-363: (I)+(O.1.30), B-364: (I)+(O.1.31), B-365: (I)+(O.1.32), B-366: (I)+(O.1.33), B-367: (I)+(O.1.34), B-368: (I)+(O.1.35), B-369: (I)+(O.1.36), B-370: (I)+(O.1.37), B-371: (I)+(O.1.38), B-372: (I)+(O.1.39), B-373: (I)+(O.1.40), B-374: (I)+(O.1.41), B-375: (I)+(O.1.42), B-376: (I)+(O.1.43), B-377: (I)+(O.1.44), B-378: (I)+(O.1.45), B-379: (I)+(O.1.46), B-380: (I)+(O.1.47), B-381: (I)+(O.1.48), B-382: (I)+(O.1.49), B-383: (I)+(O.1.50), B-384: (I)+(O.1.51), B-385: (I)+(O.1.52), B-386: (I)+(O.1.53), B-387: (I)+(O.1.54), B-388: (I)+(O.1.55), B-389: (I)+(O.1.56), B-390: (I)+(O.1.57), B-391: (I)+(O.1.58), B-392: (I)+(O.1.59), B-393: (I)+(O.1.60), B-394: (I)+(O.1.61), B-395: (I)+(O.1.62), B-396: (I)+(O.1.63), B-397: (I)+(O.1.64), B-398: (I)+(O.1.65), B-399: (I)+(O.1.66), B-400: (I)+(O.1.67), B-401: (I)+(O.1.68), B-402: (I)+(O.1.69), B-403: (I)+(O.1.70), B-404: (I)+(O.1.71), B-405: (I)+(O.1.72), B-406: (I)+(O.1.73), B-407: (I)+(O.1.74), B-408: (I)+(O.1.75), B-409: (I)+(O.1.76), B-410: (I)+(O.1.77), B-411: (I)+(O.1.78), B-412: (I)+(O.1.79), B-413: (I)+(O.1.80), B-414: (I)+(O.1.81), B-415: (I)+(O.1.82), B-416: (I)+(O.1.83), B-417: (I)+(O.1.84), B-418: (I)+(O.1.85), B-419: (I)+(O.1.86), B-420: (I)+(O.1.87), B-421: (I)+(O.1.88), B-422: (I)+(O.1.89), B-423: (I)+(O.1.90), B-424: (I)+(O.1.91), B-425: (I)+(O.2.1), B-426: (I)+(O.2.2), B-427: (I)+(O.2.3), B-428: (I)+(O.2.4), B-429: (I)+(O.2.5), B-430: (I)+(O.2.6), B-431: (I)+(O.2.7), B-432: (I)+(O.3.1), B-433: (I)+(O.3.2), B-434: (I)+(O.3.3), B-435: (I)+(O.3.4), B-436: (I)+(O.3.5), B-437: (I)+(O.3.6), B-438: (I)+(O.3.7), B-439: (I)+(O.3.8), B-440: (I)+(O.3.9), B-441: (I)+(O.3.10), B-442: (I)+(O.3.11), B-443: (I)+(O.3.12), B-444: (I)+(O.3.13), B-445: (I)+(O.3.14), B-446: (I)+(O.3.15), B-447: (I)+(O.3.16), B-448: (I)+(O.3.17), B-449: (I)+(O.3.18), B-450: (I)+(O.3.19), B-451: (I)+(O.3.20), B-452: (I)+(O.3.21), B-453: (I)+(O.3.22), B-454: (I)+(O.3.23), B-455: (I)+(O.3.24), B-456: (I)+(O.3.25), B-457: (I)+(O.3.26), B-458: (I)+(O.3.27), B-459: (I)+(O.3.28), B-460: (I)+(O.3.29), B-461: (I)+(O.3.30), B-462: (I)+(O.3.31), B-463: (I)+(O.3.32), B-464: (I)+(O.3.33), B-465: (I)+(O.3.34), B-466: (I)+(O.3.35), B-467: (I)+(O.3.36), B-468: (I)+(O.3.37), B-469: (I)+(O.3.38), B-470: (I)+(O.3.39), B-471: (I)+(O.3.40), B-472: (I)+(O.3.41), B-473: (I)+(O.3.42), B-474: (I)+(O.3.43), B-475: (I)+(O.3.44), B-476: (I)+(O.3.45), B-477: (I)+(O.3.46), B-478: (I)+(O.3.47), B-479: (I)+(O.3.48), B-480: (I)+(O.3.49), B-481: (I)+(O.3.50), B-482: (I)+(O.3.51), B-483: (I)+(O.3.52), B-484: (I)+(O.4.1), B-485: (I)+(O.4.2), B-486: (I)+(O.4.3), B-487: (I)+(O.4.4), B-488: (I)+(O.4.5), B-489: (I)+(O.4.6), B-490: (I)+(O.4.7), B-491: (I)+(O.4.8), B-492: (I)+(O.4.9), B-493: (I)+(O.4.10), B-494: (I)+(O.4.11), B-495: (I)+(O.4.12), B-496: (I)+(O.4.13), B-497: (I)+(O.4.14), B-498: (I)+(O.4.15),

B-499: (I)+(O.5.1), B-500: (I)+(O.5.2), B-501: (I)+(O.6.1), B-502: (I)+(O.6.2), B-503: (I)+(O.6.3), B-504: (I)+(O.6.4), B-505: (I)+(O.6.5), B-506: (I)+(O.7.1), B-507: (I)+(O.7.2), B-508: (I)+(O.7.3), B-509: (I)+(O.7.4), B-510: (I)+(O.7.5), B-511: (I)+(O.8.1), B-512: (I)+(O.8.2), B-513: (I)+(O.8.3), B-514: (I)+(O.8.4), B-515: (I)+(O.8.5), B-516: (I)+(O.9.1), B-517: (I)+(O.9.2), B-518: (I)+(O.9.3), B-519: (I)+(O.10.1), B-520: (I)+(O.10.2), B-521: (I)+(O.10.3), B-522: (I)+(O.10.4), B-523: (I)+(O.11.1), B-524: (I)+(O.11.2), B-525: (I)+(O.11.3), B-526: (I)+(O.11.4), B-527: (I)+(O.11.5), B-528: (I)+(O.11.6), B-529: (I)+(O.11.7), B-530: (I)+(O.11.8), B-531: (I)+(O.11.9), B-532: (I)+(O.11.10), B-533: (I)+(O.11.11), B-534: (I)+(O.11.12), B-535: (I)+(O.11.13), B-536: (I)+(O.12.1), B-537: (I)+(O.12.2), B-538: (I)+(O.12.3), B-539: (I)+(O.12.4), B-540: (I)+(O.12.5), B-541: (I)+(O.12.6), B-542: (I)+(O.13.1), B-543: (I)+(O.13.2), B-544: (I)+(O.13.3), B-545: (I)+(O.14.1), B-546: (I)+(O.14.2), B-547: (I)+(O.14.3), B-548: (I)+(O.14.4), B-549: (I)+(O.15.1), B-550: (I)+(O.15.2), B-551: (I)+(O.15.3), B-552: (I)+(O.15.4), B-553: (I)+(O.15.5), B-554: (I)+(O.15.6), B-555: (I)+(O.15.7), B-556: (I)+(O.15.8), B-557: (I)+(O.15.9), B-558: (I)+(O.15.10), B-559: (I)+(O.15.11), B-560: (I)+(O.16.1), B-561: (I)+(O.17.1), B-562: (I)+(O.18.1), B-563: (I)+(O.18.2), B-564: (I)+(O.18.3), B-565: (I)+(O.18.4), B-566: (I)+(O.18.5), B-567: (I)+(O.19.1), B-568: (I)+(O.20.1), B-569: (I)+(O.20.2), B-570: (I)+(O.20.3), B-571: (I)+(O.20.4), B-572: (I)+(O.21.1), B-573: (I)+(O.21.2), B-574: (I)+(O.21.3), B-575: (I)+(O.21.4), B-576: (I)+(O.21.5), B-577: (I)+(O.21.6), B-578: (I)+(O.21.7), B-579: (I)+(O.22.1), B-580: (I)+(O.22.2), B-581: (I)+(O.22.3), B-582: (I)+(O.22.4), B-583: (I)+(O.23.1), B-584: (I)+(O.23.2), B-585: (I)+(O.23.3), B-586: (I)+(O.23.4), B-587: (I)+(O.24.1), B-588: (I)+(O.24.2), B-589: (I)+(O.24.3), B-590: (I)+(O.24.4), B-591: (I)+(O.24.5), B-592: (I)+(O.25.1), B-593: (I)+(O.25.2), B-594: (I)+(O.26.1), B-595: (I)+(O.26.2), B-596: (I)+(O.26.3), B-597: (I)+(O.26.4), B-598: (I)+(O.26.5), B-599: (I)+(O.26.6), B-600: (I)+(O.26.7), B-601: (I)+(O.26.8), B-602: (I)+(O.26.9), B-603: (I)+(O.26.10), B-604: (I)+(O.26.11), B-605: (I)+(O.26.12), B-606: (I)+(O.26.13), B-607: (I)+(O.26.14), B-608: (I)+(O.26.15), B-609: (I)+(O.26.16), B-610: (I)+(O.26.17), B-611: (I)+(O.26.18), B-612: (I)+(O.27.1), B-613: (I)+(O.28.1), B-614: (I)+(O.28.2), B-615: (I)+(O.28.3), B-616: (I)+(O.28.4), B-617: (I)+(O.28.5), B-618: (I)+(O.28.7), B-619: (I)+(O.28.8), B-620: (I)+(O.28.9), B-621: (I)+(O.28.10), B-622: (I)+(O.28.11), B-623: (I)+(O.28.12), B-624: (I)+(O.28.13), B-625: (I)+(O.28.14), B-626: (I)+(O.28.15), B-627: (I)+(O.28.16), B-628: (I)+(O.28.17), B-629: (I)+(O.28.18), B-630: (I)+(O.28.19), B-631: (I)+(O.28.20), B-632: (I)+(O.28.21), B-633: (I)+(O.28.22), B-634: (I)+(O.28.23), B-635: (I)+(O.28.24), B-636: (I)+(O.28.25), B-637: (I)+(O.28.26), B-638: (I)+(O.28.27), B-639: (I)+(O.28.28), B-640: (I)+(O.28.29), B-641: (I)+(O.28.30), B-642: (I)+(O.28.31), B-643: (I)+(O.28.42), B-644: (I)+(O.28.43), B-645: (I)+(O.28.44), B-646: (I)+(O.28.45), B-647: (I)+(O.28.46), B-648: (I)+(O.28.47), B-649: (I)+(O.28.48), B-650: (I)+(O.28.49), B-651: (I)+(O.28.50), B-652: (I)+(O.28.51), B-653: (I)+(O.28.52), B-654: (I)+(O.28.53), B-655: (I)+(O.28.54), B-656: (I)+(O.28.55), B-657: (I)+(O.28.56), B-658: (I)+(O.28.57), B-659: (I)+(O.28.58), B-660: (I)+(O.28.59), B-661: (I)+(O.28.60), B-662: (I)+(O.28.61), B-663: (I)+(O.28.62), B-664: (I)+(O.28.63), B-665: (I)+(O.28.64), B-666: (I)+(O.28.65), B-667: (I)+(O.28.66), B-668: (I)+(O.28.67), B-669: (I)+(O.28.68), B-670: (I)+(O.28.69), B-671: (I)+(O.28.70), B-672: (I)+(O.28.71), B-673: (I)+(O.28.72), B-674: (I)+(O.28.73), B-675: (I)+(O.28.74), B-676: (I)+(O.28.75), B-677: (I)+(O.28.76), B-678: (I)+(O.28.77), B-679: (I)+(O.28.78), B-680: (I)+(O.28.79), B-681: (I)+(O.28.80), B-682: (I)+(O.28.81), B-683: (I)+(O.28.82).

The mixtures of active substances can be prepared as compositions comprising besides the active ingredients at least one inert ingredient (auxiliary) by usual means, e. g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. SYNTHESIS EXAMPLES

The compounds of the formula I can be prepared according to the methods outlined below.

I.1) Preparation of 4-(methylaminomethyl)benzonitrile

To a solution of 4-(bromomethyl)benzonitrile (49 g, 1 eq.) in tetrahydrofurane (500 mL) methylamine (194 g of a 40% solution by weight, 10 eq.) was added. The mixture was stirred overnight at room temperature. After removing the solvent under reduced pressure, an aqueous solution of sodium chloride was added and the aqueous mixture was extracted with ethyl acetate. The combined organic layer was dried with magnesium sulfate and freed from solvent.

The title compound (35.6 g) was used directly without further purification.

I.2) Preparation of N-[(4-cyanophenyl)methyl]-N-methyl-propanamide

To a solution of 4-(methylaminomethyl)benzonitrile (4.5 g, 1 eq.) in tetrahydrufurane (50 mL) propionyl chloride (3.1 g, 1.1 eq.) was added. After stirring for one minute ethyl diisopropyl-amide (6 g, 1.5 eq.) was added and the mixture was stirred an additional one hour at room temperature. The title compound was used directly without further purification.

I.3) Preparation of N-[[4-[(Z)—N'-hydroxycarbamimidoyl]phenyl]methyl]-N-methyl propanamide A solution of N-[(4-cyanophenyl)methyl]-N-methyl-propanamide (6.2 g, 1 eq.), hydroxylamine hydrochloride (3.2 g, 1.5 eq.), potassium carbonate (2.8 g, 0.7 eq.), water (15 mL) and ethanol (30 mL) was stirred overnight at room temperature. The organic solvent was removed under reduced pressure, 40 mL toluol was added, stirred and removed again. The title compound was used directly without further purification.

I.4) Preparation of N-methyl-N-[[4-[5-(trifluoromethyl)-1,2,4-oxadiazol-3-yl]phenyl]methyl]propanamide To a solution of N-[[4-[(Z)—N'-hydroxycarbamimidoyl]phenyl]methyl]-N-methyl-propanamide (7.2 g, 1 eq.) in tetrahydrofurane (100 mL) and N,N-dimethylformamide (20 mL) gradually trifluoroacetic anhydride (12 mL) was added. The mixture was stirred at 50° C. until HPLC indicated complete conversion of the starting material. In case the conversion was not complete more trifluoroacetic anhydride was added. The solvent was removed under reduced pressure, water was added and the aqueous layer was extracted with etylacetate. The organic layer was poured into dichloromethane and washed with an aqueous solution of hydrochloric acid (1N solution) followed by an aqueous solution of sodium hydrogen carbonate. The organic layer was dried with magnesium sulfate and the solvent was removed under reduced pressure. The crude product was purified by column chromatography (cyclohexane: ethyl acetate) to afford the desired product as a colorless solid (5 g, 52%). Melting point: 30° C., LC/MS: Retention time ($R_t$) 1.146 min, $^1$H NMR (400 MHz, CDCl$_3$): δ [ppm]=8.1 (2H), 7.4 (2H), 4.7 (2H), 3.0 (3H), 2.5 (2H), 1.2 (3H).

I.5) Preparation of N-methyl-N-[[4-[5-(trifluoromethyl)-1,2,4-oxadiazol-3-yl]phenyl]methyl]propanethioamide (Ex-7, Example not According to the Invention)

To a solution of N-methyl-N-[[4-[5-(trifluoromethyl)-1,2,4-oxadiazol-3-yl]phenyl]methyl]-propanamide (0.20 g, 1 eq.) in 3.7 mL toluene was added diphosphorus pentasulfide (156 mg, 1.1 eq.). The mixture was heated for 4 hours at 110° C. Water was added and the aqueous phase was extracted with ethyl acetate. The separated organic layer was washed with saturated sodium chloride solution and dried with magnesium sulfate. Then the solvent was removed under reduced pressure and the crude product was purified by column chromatography (cyclohexane, ethyl acetate) to afford the desired product as a colorless solid (152 mg, 69%). LC/MS: Retention time ($R_t$) 1.298 min, $^1$H NMR (500 MHz, CDCl$_3$): δ [ppm]=8.05-8.18 (2H), 7.27 & 7.43 (2H), 5.45 & 4.95 (2H), 3.48 & 3.25 (3H), 2.89 (2H), 1.38 (3H).

I.6) Preparation of N'-hydroxy-4-(methylaminomethyl)benzamidine

To a solution of 4-(methylaminomethyl)benzonitrile (61.4 g, 1 eq.) and trimethylamine (106 g, 2.5 eq.) in ethanol (500 mL) hydroxylamine hydrochloride (58.4 g, 2 eq.) was added. The mixture was heated overnight at 80° C. After cooling to room temperature, the solvent was removed under reduced pressure. The title compound was used directly without further purification.

I.7) Preparation of N-methyl-1-[4-[5-(trifluoromethyl)-1,2,4-oxadiazol-3-yl]phenyl]methanamine A solution of N'-hydroxy-4-(methylaminomethyl)benzamidine (25.5 g, 1 eq.) in dichloromethane (200 mL) was treated with trifluoroacetic anhydride (119 g, 4 eq.). The resulting mixture was stirred overnight at ambient temperature, before it was diluted with water and washed with dichloromethane. The combined organic layer was washed with an aqueous solution of sodium hydrogencarbonate, dried with magnesium sulfate and freed from solvent. The residue (dark oil) was used directly without further purification (42.4 g).

I.8) Preparation of N-methyl-N-[[4-[5-(trifluoromethyl)-1,2,4-oxadiazol-3-yl]phenyl]methyl]ethanesulfonamide (Ex-18, Example not According to the Invention)

To a solution of N-methyl-1-[4-[5-(trifluoromethyl)-1,2,4-oxadiazol-3-yl]phenyl]methanamine (400 mg, 1.0 eq.) in dichloromethane (2 mL) was added trimethylamine (377 mg, 2.4 eq.) and ethanesulfonyl chloride (240 mg, 1.2 eq.) dropwise. The mixture was stirred at room temperature until HPLC indicated complete conversion of the starting material. After washing with an aqueous solution of hydrochloric acid (1N) the organic layer was dried with magnesium sulfate and the solvent was removed under reduced pressure. The crude product was purified by column chromatography (cyclohexane:ethyl acetate) to afford the desired product as a colorless solid (130 mg, 24%). Melting point: 53° C., LC/MS: Retention time 1.163 min., $^1$H NMR (400 MHz, CDCl$_3$): δ [ppm]=8.1 (2H), 7.5 (2H), 4.4 (2H), 3.1 (2H), 2.8 (3H), 1.4 (3H).

I.9) Preparation of 4-[1-(methylamino)ethyl]benzonitrile

To a solution of 4-(1-bromoethyl)benzonitrile (3.2 g, 1 eq.) in tetrahydrofuran (50 mL) methylamine (11.8 g of a 40% solution by weight, 10 eq.) was added. The mixture was stirred overnight at room temperature. After removing the solvent under reduced pressure, an aqueous solution of sodium chloride was added and the aqueous mixture was extracted with ethyl acetate. The combined organic layer was dried over magnesium sulfate and freed from solvent. The title compound (2.2 g) was used directly without further purification.

I.10) Preparation of N'-hydroxy-4-[1-(methylamino)ethyl]benzamidine

A solution of 4-[1-(methylamino)ethyl]benzonitrile (2.2 g, 1 eq.), hydroxylamine hydrochloride (1.5 g, 2 eq.), triethylamine (2.8 g, 2.5 eq.) and ethanol (40 mL) was stirred overnight at room temperature. The organic solvent was removed under reduced pressure. The title compound (2.1 g) was used directly without further purification.

I.11) Preparation of N-methyl-1-[4-[5-(trifluoromethyl)-1,2,4-oxadiazol-3-yl]phenyl]ethanamine A solution of N'-hydroxy-4-[1-(methylamino)ethyl]benzamidine (2.1 g, 1 eq.) in dichloromethane (30 mL) was treated with trifluoroacetic anhydride (8.1 g, 5 eq.). The resulting mixture was stirred overnight at ambient temperature, before it was diluted with water and washed with dichloromethane. The combined organic layer was washed with an aqueous solution of sodium hydrogencarbonate, dried with magnesium sulfate and freed from solvent. The residue (2.46 g) was used directly without further purification.

I.12) Preparation of N-methyl-N-[1-[4-[5-(trifluoromethyl)-1,2,4-oxadiazol-3-yl]phenyl]ethyl]propanamide To a solution of N-methyl-1-[4-[5-(trifluoromethyl)-1,2,4-oxadiazol-3-yl]phenyl]ethanamine (0.35 g, 1 eq.) in dichloromethane (5 mL) and triethylamine (0.2 g, 2.2 eq.) gradually propionyl chloride (0.91 g, 1.1 eq.) was added. The mixture was stirred at room temperature until HPLC indicated complete conversion of the starting material. The solvent was removed under reduced pressure, water was added and the aqueous layer was extracted with ethyl acetate. The organic layer was poured into dichloromethane and washed with an aqueous solution of hydrochloric acid (1N solution) followed by an aqueous solution of sodium hydrogen carbonate. The organic layer was dried over magnesium sulfate and the solvent was removed under reduced pressure. The crude product was purified by column chromatography to afford the desired product as a colorless oil (0.23 g, 78%). LC/MS: Retention time ($R_t$) 1.19 min, $^1$H NMR (400 MHz, CDCl$_3$): δ [ppm]=8.1 (2H), 7.4 (2H), 6.14 (1H), 2.7 (3H), 2.4 (2H), 1.6 (1H), 1.5 (2H) 1.2 (3H).

I.13) Preparation of N-methyl-N-[1-[4-[5-(trifluoromethyl)-1,2,4-oxadiazol-3-yl]phenyl]ethyl]propanethioamide (Ex-8)

To a solution of N-methyl-N-[1-[4-[5-(trifluoromethyl)-1,2,4-oxadiazol-3-yl]phenyl]ethyl]-propanamide (0.20 g, 1 eq.) in 3.6 mL toluene was added diphosphorus pentasulfide (149 mg, 1.1 eq.). The mixture was heated for 4 hours at 110° C. Water was added and the aqueous phase was extracted with ethyl acetate. The separated organic layer was washed with saturated sodium chloride solution and dried with magnesium sulfate. The solvent was removed under reduced pressure and the crude product was purified by column chromatography (cyclohexane, ethyl acetate) to afford the desired product as a colorless solid (167 mg, 95%). LC/MS: Retention time ($R_t$) 1.35 min, $^1$H NMR (500 MHz, CDCl$_3$): δ [ppm]=8.18 (d, 2H), 7.49 (d, 2H), 7.46 (q, 1H), 2.80-3.21 (5H), 1.31-1.78 (6H).

I.14) Preparation of N-[1-(4-cyanophenyl)ethyl]methanesulfonamide

To a solution of 4-(1-aminoethyl)benzonitrile (400 mg, 1.0 eq.) in ethanol (5 mL) was added trimethylamine (553 mg, 2 eq.) and methanesulfonyl chloride (313 mg, 1 eq.) dropwise. The mixture was stirred at room temperature until HPLC indicated complete conversion of the starting material. After washing with an aqueous solution of hydrochloric acid (1N) the organic layer was dried with magnesium sulfate and the solvent was removed under reduced pressure. The title compound (0.61 g) was used directly without further purification.

I.15) Preparation of N'-hydroxy-4-[1-(methanesulfonamido)ethyl]benzamidine

A solution of N-[1-(4-cyanophenyl)ethyl]methanesulfonamide (0.40 g, 1 eq.), hydroxylamine hydrochloride (0.25 g, 2 eq.), triethylamine (0.36 g, 2 eq.) and ethanol (5 mL) was stirred overnight at room temperature. The organic solvent was removed under reduced pressure. The title compound (0.46 g) was used directly without further purification.

I.16) Preparation of N-[1-[4-[5-(trifluoromethyl)-1,2,4-oxadiazol-3-yl]phenyl]ethyl]methanesulfonamide (Ex-30)

A solution of N'-hydroxy-4-[1-(methanesulfonamido) ethyl]benzamidine (450 mg, 1.0 eq.) in methylene chloride (10 mL) was treated with trifluoroacetic anhydride (1.1 g, eq.). The resulting mixture was stirred overnight at ambient temperature, before it was diluted with water and washed with dichloromethane. The combined organic layer was washed with an aqueous solution of sodium hydrogencarbonate, dried with magnesium sulfate and freed from solvent. The and the crude product was purified by column chromatography (0.10 g, 16%) to afford the desired product. L/MS: Retention time 1.09 min., $^1$H NMR (400 MHz, CDCl$_3$): δ [ppm]=8.15 (d, 2H), 7.51 (d, 2H), 4.75 (q, 1H),4.64 (s, 1H), 2.75 (s, 3H), 1.56 (d, 3H).

Compounds Ex-1 to Ex-47 in Table I were prepared in analogy to the procedures described above.

TABLE I

Compounds Ex-1 to Ex-47 of formula I.Ex, wherein the meaning of $R^1$, $R^2$, $R^3$, $R^4$ and L is as defined in each line.

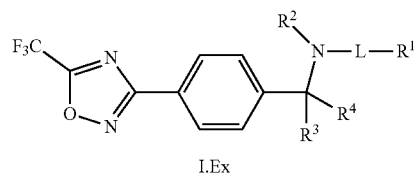

I.Ex

| Ex. no | $R^1$ | $R^2$ | $R^3/R^4$ | L | HPLC $R_t$ (min)** | Melting point (° C.) |
|---|---|---|---|---|---|---|
| Ex-1 | CH$_3$ | CH$_3$ | H/CH$_3$ | —C(═S)— | 1.28 | 62 |
| Ex-2 | iso-propyl | CH$_3$ | H/CH$_3$ | —C(═S)— | 1.42 | 77 |
| Ex-3* | ethyl | iso-propyl | H/H | —C(═S)— | 1.38 | — |
| Ex-4 | propyl | CH$_3$ | H/CH$_3$ | —C(═S)— | 1.41 | — |
| Ex-5* | propyl | CH$_3$ | H/H | —C(═S)— | 1.36 | — |
| Ex-6* | 2-butyl | CH$_3$ | H/H | —C(═S)— | 1.42 | — |
| Ex-7* | ethyl | CH$_3$ | H/H | —C(═S)— | 1.30 | 63 |
| Ex-8 | ethyl | CH$_3$ | H/CH$_3$ | —C(═S)— | 1.35 | — |
| Ex-9* | tert-butyl | iso-propyl | H/H | —C(═S)— | 1.49 | — |
| Ex-10* | iso-propyl | CH$_3$ | H/H | —C(═S)— | 1.33 | 73 |
| Ex-11* | 3-pentyl | CH$_3$ | H/H | —C(═S)— | 1.47 | 71 |
| Ex-12* | CH$_3$ | allyl | H/H | —C(═S)— | 1.32 | — |
| Ex-13* | CH$_3$ | CH$_3$ | H/H | —C(═S)— | 1.22 | 86 |
| Ex-14* | CH$_3$ | iso-propyl | H/H | —SO$_2$— | 1.22 | — |
| Ex-15* | propyl | iso-propyl | H/H | —SO$_2$— | 1.34 | — |
| Ex-16* | ethyl | iso-propyl | H/H | —SO$_2$— | 1.29 | — |
| Ex-17* | CH$_3$ | CH$_3$ | H/H | —SO$_2$— | 1.11 | — |
| Ex-18* | ethyl | CH$_3$ | H/H | —SO$_2$— | 1.16 | 53 |
| Ex-19* | propyl | CH$_3$ | H/H | —SO$_2$— | 1.25 | 91 |

TABLE I-continued

Compounds Ex-1 to Ex-47 of formula I.Ex, wherein the meaning of $R^1$, $R^2$, $R^3$, $R^4$ and L is as defined in each line.

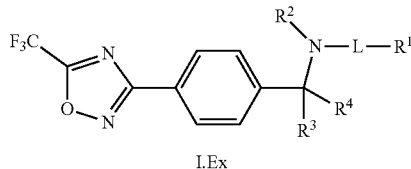

I.Ex

| Ex. no | $R^1$ | $R^2$ | $R^3/R^4$ | L | HPLC $R_t$ (min)** | Melting point (° C.) |
|---|---|---|---|---|---|---|
| Ex-20* | propyl | ethyl | H/H | —SO$_2$— | 1.27 | 83-88 |
| Ex-21* | CH$_3$ | ethyl | H/H | —SO$_2$— | 1.17 | 64-67 |
| Ex-22* | iso-propyl | CH$_3$ | H/H | —SO$_2$— | 1.22 | 124-129 |
| Ex-23* | ethyl | ethyl | H/H | —SO$_2$— | 1.22 | 96 |
| Ex-24* | iso-propyl | iso-propyl | H/H | —SO$_2$— | 0.98 | 137 |
| Ex-25* | CH$_3$ | 3-pentyl | H/H | —SO$_2$— | 1.32 | — |
| Ex-26* | CH$_3$ | cyclopropyl | H/H | —SO$_2$— | 1.18 | 88-89 |
| Ex-27* | ethyl | cyclopropyl | H/H | —SO$_2$— | 1.22 | 87 |
| Ex-28* | propyl | cyclopropyl | H/H | —SO$_2$— | 1.28 | 89 |
| Ex-29* | 2-butyl | CH$_3$ | H/H | —SO$_2$— | 1.30 | 88 |
| Ex-30 | CH$_3$ | H | H/CH$_3$ | —SO$_2$— | 1.09 | — |
| Ex-31 | ethyl | H | H/CH$_3$ | —SO$_2$— | 1.13 | — |
| Ex-32 | 3-pentyl | H | H/CH$_3$ | —SO$_2$— | 1.29 | — |
| Ex-33* | 2,2,2-trifluoroethyl | CH$_3$ | H/H | —SO$_2$— | 1.27 | 113-115 |
| Ex-34* | 2,2-difluoropropyl | CH$_3$ | H/H | —SO$_2$— | 1.26 | 93 |
| Ex-35* | 2,2,2-trifluoro-1-methyl-ethyl | CH$_3$ | H/H | —SO$_2$— | 1.29 | 110 |
| Ex-36* | 2,2-difluoroethyl | CH$_3$ | H/H | —SO$_2$— | 1.23 | 92 |
| Ex-37* | 2,2,2-trifluoroethyl | ethyl | H/H | —SO$_2$— | 1.30 | 97 |
| Ex-38* | 2,2,2-trifluoro-1-methyl-ethyl | ethyl | H/H | —SO$_2$— | 1.32 | 110 |
| Ex-39* | 2,2-difluoroethyl | ethyl | H/H | —SO$_2$— | 1.26 | 76 |
| Ex-40* | 2,2-difluoropropyl | ethyl | H/H | —SO$_2$— | 1.30 | 88 |
| Ex-41* | 2,2,2-trifluoroethyl | cyclopropyl | H/H | —SO$_2$— | 1.32 | 108 |
| Ex-42* | 2,2,2-trifluoro-1-methyl-ethyl | cyclopropyl | H/H | —SO$_2$— | 1.34 | 83 |
| Ex-43* | 2,2-difluoroethyl | cyclopropyl | H/H | —SO$_2$— | 1.25 | 62 |
| Ex-44* | 2,2-difluoropropyl | cyclopropyl | H/H | —SO$_2$— | 1.28 | 90 |
| Ex-45* | 2,2,2-trifluoroethyl | CH$_3$ | H/CH$_3$ | —SO$_2$— | 1.27 | 124 |
| Ex-46* | 2,2-difluoroethyl | CH$_3$ | H/CH$_3$ | —SO$_2$— | 1.26 | 96 |
| Ex-47* | 2,2,2-trifluoroethyl | allyl | H/H | —SO$_2$— | 1.33 | 73 |

*compound not according to the invention
**HPLC: High Performance Liquid Chromatography; HPLC-column Kinetex XB C18 1.7μ (50 × 2.1 mm); eluent: acetonitrile/water + 0.1% trifluoroacetic acid (gradient from 5:95 to 100:0 in 1.5 min at 60° C., flow gradient from 0.8 to 1.0 ml/min in 1.5 min).
MS: Quadrupol Electrospray Ionisation, 80 V (positive mode). $R_t$: retention time in minutes.

II. BIOLOGICAL EXAMPLES FOR FUNGICIDAL ACTIVITY

The fungicidal action of the compounds of formula I was demonstrated by the following experiments: The spray solutions were prepared in several steps: The stock solution were prepared by mixing acetone and/or dimethylsulfoxide and the wetting agent/emulsifier Wettol, which is based on ethoxylated alkylphenoles, in a relation (volume) solvent-emulsifier of 99 to 1. This mixture was added to 25 mg of the compound to give a total of 5 mL. Water was then added to total volume of 100 mL. This stock solution was diluted with the described solvent-emulsifier-water mixture to the given concentration.

II.1) Curative Control of Soy Bean Rust on Soy Beans Caused by *Phakopsora pachyrhizi*

Leaves of pot-grown soy bean seedlings were inoculated with spores of *Phakopsora pachyrhizi*. To ensure the success of the artificial inoculation, the plants were transferred to a humid chamber with a relative humidity of about 95% and 20 to 24° C. for 24 hours. The next day the plants were cultivated for 3 days in a greenhouse chamber at 23 to 27° C. and a relative humidity between 60 and 80%. Then the plants were sprayed to run-off with an aqueous suspension, containing the concentration of active ingredient or their mixture as described below. The plants were allowed to air-dry. Then the trial plants were cultivated for 14 days in a greenhouse chamber at 23 to 27° C. and a relative humidity between 60 and 80%. The extent of fungal attack on the leaves was visually assessed as % diseased leaf area.

In this test, the plants which had been treated with 32 ppm of the active compounds Ex-1, Ex-2, Ex-3, Ex-4, Ex-5, Ex-6, Ex-7, Ex-10, Ex-11, Ex-12 and Ex-13 showed a diseased leaf area of at most 20%, whereas the untreated plants showed 90% diseased leaf area.

In this test, the plants which had been treated with 32 ppm of the active compounds Ex-14, Ex-16, Ex-17, Ex-18 and Ex-19 showed a diseased leaf area of at most 2%, whereas the untreated plants showed 100% diseased leaf area.

In this test, the plants which had been treated with 63 ppm of the active compounds Ex-20, Ex-21, Ex-22, Ex-23, Ex-26, Ex-27, Ex-29, Ex-30, Ex-31, Ex-32, Ex-35, Ex-36, Ex-37, Ex-39, Ex-40, Ex-41, Ex-43, Ex-44 and Ex-46 showed a diseased leaf area of at most 16%, whereas the untreated plants showed 90% diseased leaf area.

II.2) Protective Control of Soy Bean Rust on Soy Beans Caused by *Phakopsora pachyrhizi*

Leaves of pot-grown soy bean seedlings were sprayed to run-off with an aqueous suspension, containing the concentration of active ingredient or their mixture as described below. The plants were allowed to air-dry. The trial plants were cultivated for 2 day in a greenhouse chamber at 23 to 27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20 to 24° C. for 24 hours. The trial plants were cultivated for fourteen days in a greenhouse chamber at 23 to 27° C. and a relative humidity between 60 and 80%. The extent of fungal attack on the leaves was visually assessed as % diseased leaf area.

In this test, the plants which had been treated with 32 ppm of the active compounds Ex-1, Ex-2, Ex-3, Ex-4, Ex-5, Ex-6, Ex-7, Ex-8, Ex-9, Ex-10, Ex-11, Ex-12, Ex-13 Ex-14, Ex-15, Ex-16, Ex-17, Ex-18 and Ex-19 showed a diseased leaf area of at most 5%, whereas the untreated plants showed 100% diseased leaf area.

In this test, the plants which had been treated with 63 ppm of the active compounds Ex-20, Ex-21, Ex-22, Ex-23, Ex-25, Ex-26, Ex-27, Ex-28, Ex-29, Ex-30, Ex-31, Ex-32, Ex-35, Ex-36, Ex-37, Ex-38, Ex-39, Ex-40, Ex-41, Ex-42, Ex-43, Ex-44, Ex-45 and Ex-46 showed a diseased leaf area of at most 7%, whereas the untreated plants showed 90% diseased leaf area.

II.3) Curative Control of Brown Rust on Wheat Caused by *Puccinia recondita*

The first two developed leaves of pot-grown wheat seedling were dusted with spores of *Puccinia recondita*. To ensure the success the artificial inoculation, the plants were transferred to a humid chamber without light and a relative humidity of 95 to 99% and 20 to 24° C. for 24 hours. The next day the plants were cultivated for 3 days in a greenhouse chamber at 20 to 24° C. and a relative humidity between 65 and 70%. Then the plants were sprayed to run-off with an aqueous suspension, containing the concentration of active ingredient or their mixture as described below. The plants were allowed to air-dry. Then the trial plants were cultivated for 8 days in a greenhouse chamber at 20 to 24° C. and a relative humidity between 65 and 70%. The extent of fungal attack on the leaves was visually assessed as % diseased leaf area.

In this test, the plants which had been treated with 63 ppm of the active compounds Ex-1, Ex-2, Ex-3, Ex-5, Ex-6, Ex-7, Ex-8, Ex-10, Ex-11, Ex-13, Ex-14, Ex-17 and Ex-18 showed a diseased leaf area of at most 15%, whereas the untreated plants showed 90% diseased leaf area.

In this test, the plants which had been treated with 63 ppm of the active compounds Ex-21, Ex-22, Ex-23, Ex-26, Ex-27, Ex-29, Ex-30, Ex-31, Ex-36 and Ex-39 showed a diseased leaf area of at most 9%, whereas the untreated plants showed 90% diseased leaf area.

II.4) Preventative Control of Brown Rust on Wheat Caused by *Puccinia recondita*

The first two developed leaves of pot-grown wheat seedling were sprayed to run-off with an aqueous suspension, containing the concentration of active ingredient or their mixture as described below. The next day the plants were inoculated with spores of *Puccinia recondita*. To ensure the success the artificial inoculation, the plants were transferred to a humid chamber without light and a relative humidity of 95 to 99% and 20 to 24° C. for 24 hours. Then the trial plants were cultivated for 6 days in a greenhouse chamber at 20-24° C. and a relative humidity between 65 and 70%. The extent of fungal attack on the leaves was visually assessed as % diseased leaf area.

In this test, the plants which had been treated with 63 ppm of the active compounds Ex-14, Ex-16, Ex-17, Ex-18 and Ex-19 showed a diseased leaf area of at most 5%, whereas the untreated plants showed 80% diseased leaf area.

In this test, the plants which had been treated with 63 ppm of the active compounds Ex-20, Ex-21, Ex-22, Ex-23, Ex-25, Ex-26, Ex-27, Ex-28, Ex-29, Ex-30, Ex-31, Ex-36, Ex-37, Ex-39, Ex-40 and Ex-43 showed a diseased leaf area of at most 15%, whereas the untreated plants showed 90% diseased leaf area.

The invention claimed is:

1. A compound of the formula I, or an N-oxide, or an agriculturally acceptable salt thereof;

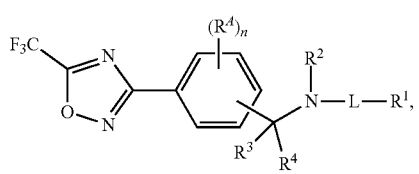

wherein:

$R^A$ is independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;

n is 0, 1 or 2;

L is —(C=S)—;

$R^1$ is $C_1$-$C_6$-alkyl or $C_1$-$C_6$-alkoxy; wherein any of the aliphatic groups are unsubstituted or substituted with 1, 2, 3, 4, 5 or up to the maximum possible number of identical or different radicals selected from the group consisting of hydroxy, cyano, $C_1$-$C_6$-alkyl, $C_1$-$C_6$-alkoxy and $C_3$-$C_8$-cycloalkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_8$-cycloalkyl, $C_3$-$C_8$-cycloalkenyl, $C_3$-$C_8$-cycloalkyl-$C_1$-$C_4$-alkyl, phenyl-$C_1$-$C_4$-alkyl, phenyl, C(=O)—($C_1$-$C_6$-alkyl) or C(=O)—($C_1$-$C_6$-alkoxy); and wherein any of the aliphatic or cyclic groups are unsubstituted or substituted with 1, 2, 3 or up to the maximum possible number of identical or different radicals selected from the group consisting of halogen, hydroxy, cyano, $C_1$-$C_6$-alkyl, $C_1$-$C_6$-alkoxy and $C_3$-$C_8$-cycloalkyl;

$R^3$, $R^4$ independently of each other are selected from the group consisting of hydrogen, halogen, cyano, $C_1$-$C_4$-alkyl, $C_1$-$C_4$-alkenyl, $C_1$-$C_4$-alkynyl, $C_1$-$C_4$-haloalkyl and $C_1$-$C_4$-alkoxy;

or $R^3$ and $R^4$ together with the carbon atom to which they are bound form a saturated 3- to 7-membered carbocycle or a saturated 3- to 6-membered heterocycle; wherein the saturated heterocycle includes beside carbon atoms 1, 2 or 3 heteroatoms independently selected from the group consisting of N, O and S as ring member atoms; and wherein said N ring member atom is substituted with the group $R^N$; wherein $R^N$ is hydrogen, $C_1$-$C_6$-alkyl or halogen;

and wherein said S ring member atom is unsubstituted or substituted with 1 or 2 oxo radicals; and wherein one or two $CH_2$ groups of the saturated carbocycle or of the saturated heterocycle may be replaced by one or two groups independently selected from —C(=O)— and —C(=S)—; and wherein the carbon ring member atoms of the saturated carbocycle or of the saturated heterocycle are unsubstituted or substituted with a total number of 1, 2, 3, 4 or up to the maximum possible number of identical or different radicals selected from the group consisting of halogen, cyano, $C_1$-$C_6$-alkyl, $C_1$-$C_6$-alkoxy and $C_3$-$C_8$-cycloalkyl;

with the exception of compounds of the formula I wherein $R^3$ and $R^4$ both are hydrogen.

2. The compound of claim 1 having formula I.1, or an N-oxide, or an agriculturally acceptable salt thereof

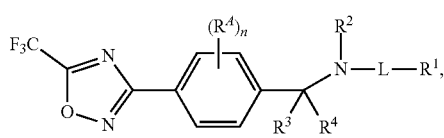

I.1 wherein n is 0 or 1.

3. The compound of claim 1, wherein n is 0.

4. The compound of claim 1, wherein $R^3$ and $R^4$ are independently selected from the group consisting of hydrogen, halogen, $C_1$-$C_6$-alkyl and $C_1$-$C_6$-haloalkyl; or $R^3$ and $R^4$ together with the carbon atom to which they are bound form a cyclopropyl ring; with the exception of compounds of the formula I wherein $R^3$ and $R^4$ both are hydrogen.

5. The compound of claim 1, wherein $R^3$ is hydrogen and $R^4$ is methyl or trifluoromethyl.

6. The compound of claim 1, wherein $R^3$ and $R^4$ together with the carbon atom to which they are bound form a cyclopropyl ring.

7. The compound of claim 1, wherein $R^1$ is $C_1$-$C_6$-alkyl; unsubstituted or substituted with 1, 2, 3 or up to the maximum possible number of identical or different radicals selected from the group consisting of $C_1$-$C_6$-alkoxy and $C_3$-$C_8$-cycloalkyl.

8. The compound of claim 1, wherein $R^2$ is hydrogen, $C_1$-$C_6$-alkyl, $C_2$-$C_6$-alkenyl, $C_3$-$C_8$-cycloalkyl, $C_3$-$C_8$-cycloalkyl-$C_1$-$C_4$-alkyl or phenyl; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy.

9. The compound of claim 1, wherein $R^2$ is hydrogen, $C_1$-$C_6$-alkyl, $C_1$-$C_6$-alkenyl, ethynyl, propargyl, $C_3$-$C_8$-cycloalkyl, $C_3$-$C_8$-cycloalkyl-$C_1$-$C_4$-alkyl or phenyl; and wherein any of the aliphatic or cyclic groups are unsubstituted or substituted with 1, 2, 3, 4 or up to the maximum possible number of identical or different radicals selected from the group consisting of halogen and $C_1$-$C_6$-alkyl; and $R^1$ is $C_1$-$C_6$-alkyl.

10. An agrochemical composition, which comprises an auxiliary and at least one compound of the formula I, or an N-oxide, or an agriculturally acceptable salt thereof, as defined in claim 1.

11. The agrochemical composition of claim 10, wherein the auxiliary is selected from the group of ionic or non-ionic surfactants.

12. Seed treated with the composition of claim 10, wherein the amount of the compound of the formula I, or an N-oxide, or an agriculturally acceptable salt thereof, is from 0.1 g to 10 kg per 100 kg of seed.

13. A method for combating phytopathogenic harmful fungi, which process comprises treating the fungi, the plants, the soil or seeds to be protected against fungal attack, with an effective amount of at least one compound of formula I, or an N-oxide, or an agriculturally acceptable salt thereof, as defined in claim 1.

14. The method of claim 13, wherein the compound of formula I is a compound of formula I.1, or an N-oxide, or an agriculturally acceptable salt thereof

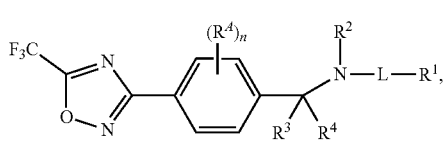

I.1 wherein n is 0 or 1.

15. The method of claim 13, wherein $R^3$ and $R^4$ are independently selected from the group consisting of hydrogen, halogen, $C_1$-$C_6$-alkyl and $C_1$-$C_6$-haloalkyl; or $R^3$ and $R^4$ together with the carbon atom to which they are bound form a cyclopropyl ring; with the exception of compounds of the formula I wherein $R^3$ and $R^4$ both are hydrogen.

16. The method of claim 13, wherein $R^3$ is hydrogen and $R^4$ is methyl or trifluoromethyl.

17. The method of claim 13, wherein $R^3$ and $R^4$ together with the carbon atom to which they are bound form a cyclopropyl ring.

18. The method of claim 13, wherein $R^1$ is $C_1$-$C_6$-alkyl; unsubstituted or substituted with 1, 2, 3 or up to the maximum possible number of identical or different radicals selected from the group consisting of $C_1$-$C_6$-alkoxy and $C_3$-$C_8$-cycloalkyl.

19. The method of claim 13, wherein $R^2$ is hydrogen, $C_1$-$C_6$-alkyl, $C_2$-$C_6$-alkenyl, $C_3$-$C_8$-cycloalkyl, $C_3$-$C_8$-cycloalkyl-$C_1$-$C_4$-alkyl or phenyl; and wherein any of the aliphatic or cyclic groups are unsubstituted or substituted with 1, 2, 3, 4 or up to the maximum possible number of identical or different radicals selected from the group consisting of halogen, cyano, $C_1$-$C_6$-alkyl and $C_1$-$C_6$-alkoxy.

20. The method of claim 13, wherein $R^2$ is hydrogen, $C_1$-$C_6$-alkyl, $C_1$-$C_6$-alkenyl, ethynyl, propargyl, $C_3$-$C_8$-cycloalkyl, $C_3$-$C_8$-cycloalkyl-$C_1$-$C_4$-alkyl or phenyl; and wherein any of the aliphatic or cyclic groups are unsubstituted or substituted with 1, 2, 3, 4 or up to the maximum possible number of identical or different radicals selected from the group consisting of halogen and $C_1$-$C_6$-alkyl; and $R^1$ is $C_1$-$C_6$-alkyl.

* * * * *